United States Patent [19]

Nakamura

[11] Patent Number: 4,878,113
[45] Date of Patent: Oct. 31, 1989

[54] ENDOSCOPE APPARATUS
[75] Inventor: Kazunari Nakamura, Hachioji, Japan
[73] Assignee: Olympus Optical Co., Ltd., Tokyo, Japan
[21] Appl. No.: 230,540
[22] Filed: Aug. 10, 1988
[30] Foreign Application Priority Data
Aug. 11, 1987 [JP] Japan .................................. 62-200294
Feb. 8, 1988 [JP] Japan .................................. 63-026839
[51] Int. Cl.$^4$ ............................. A61B 1/04; A61B 1/06
[52] U.S. Cl. ........................................... 358/98; 128/6; 358/47; 358/113
[58] Field of Search ................. 358/98, 42, 113; 128/6

[56] References Cited
U.S. PATENT DOCUMENTS 3,770,887 11/1973 Van Buskirk ........................ 358/42
4,621,284 11/1986 Nishioka .............................. 358/98
4,717,952 1/1988 Kohayakawa et al. .............. 358/113

FOREIGN PATENT DOCUMENTS 3033 2/1981 Japan .
136714 7/1985 Japan .
149267 8/1985 Japan .
149269 8/1985 Japan .
114543 5/1987 Japan .
151705 9/1987 Japan .

Primary Examiner—Howard W. Britton
Attorney, Agent, or Firm—Armstrong, Nikaido, Marmelstein, Kubovcik & Murray

[57] ABSTRACT

The endoscope apparatus comprises an endoscope body having an elongate insertable part having an observing window in the tip part and an image forming optical system forming an object image by receiving a light returning from the object and entering through the observing window; an imaging device imaging the object image formed by the image forming optical system; a first wavelength range separating device separating the object image into images in a plurality of wavelength ranges in response to a simultaneous type color imaging system; a second wavelength range separating device separating the object image into images in a plurality of wavelength ranges of a combinations different from the first wavelength range separating means; a signal processing device processing signals for the imaging device in response to the respective wavelength ranges separated by the first wavelength range separating means or the second wavelength range separating means; and a switching device switching the first wavelength range separating device and the second wavelength range separating device. All pixels of the imaging device corresponding to the second wavelength range separating device are included in all pixels of the imaging device corresponding to the first wavelength range separating device.

28 Claims, 24 Drawing Sheets

| Cy | G | Cy | G |
| --- | --- | --- | --- |
| Ye | G | Ye | G |
| Cy | G | Cy | G |
| G | Ye | G | Ye |
| | | | |

FIG.24
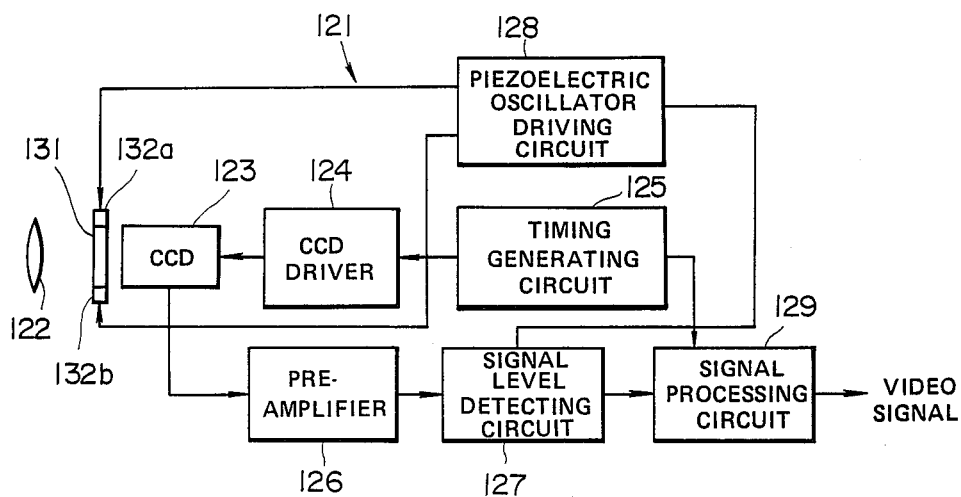
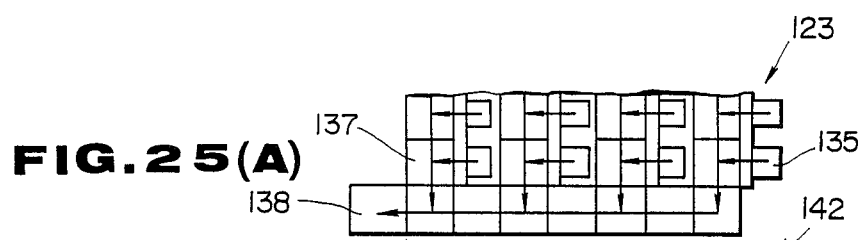
FIG.25(A)
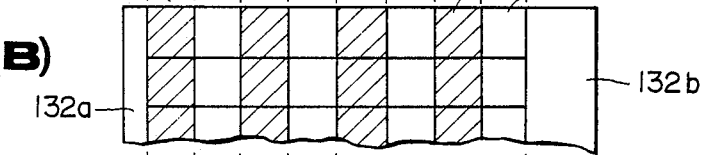
FIG.25(B)
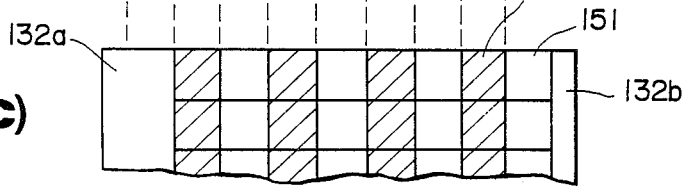
FIG.25(C)

FIG. 28(B) TIME a

FIG. 28(C) TIME b

FIG. 28(D) TIME c

FIG. 30
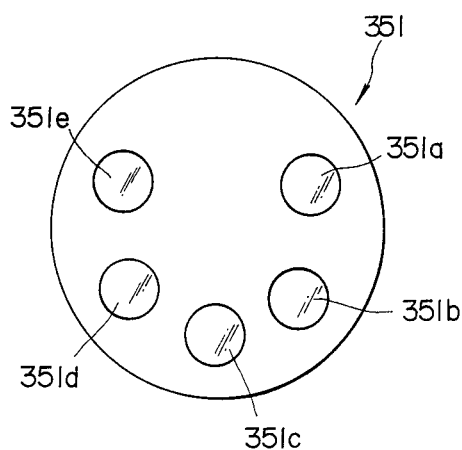
FIG. 31
| Cy | G | Cy | G |
|----|---|----|----|
| Ye | G | Ye | G |
| Cy | G | Cy | G |
| G | Ye | G | Ye |
| Cy | G | Cy | G |
| Ye | G | Ye | G |
202
FIG. 32
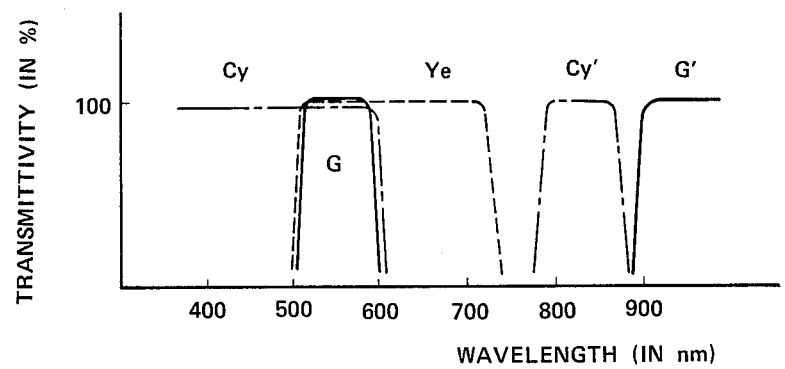

ENDOSCOPE APPARATUS

BACKGROUND OF THE INVENTION

1. Field of the Invention

This invention relates to an endoscope apparatus whereby a color picture image in a general visible range and a special picture image by a combination of specific wavelength range can be observed.

2. Related Art Statement

Recently, there is extensively utilized an endoscope whereby an organ within a body cavity or the like can be observed by inserting an elongate insertable part into a cavity of a living body or mechanical component part or, as required, various curing treatments can be made by using a treating tool inserted through a treating tool channel.

Also, there are suggested various electronic endoscopes wherein such solid state imaging device as a change coupled device (CCD) is used for an imaging means.

Now, in case an object is to be observed by using the above mentioned endoscope and particularly, in case an affected part and a normal part are to be distinguished from each other within a living body, it will be necessary to sense (recognize) a delicate tone difference. However, in case the tone variation in the observed part is delicate, a high knowledge and experience will be required to sense this delicate difference and further a long time will be required until it is sensed and, even if attentions are concentrated while sensing, it has been difficult to always judge properly.

In order to cope with these problems, conventionally, for example, as shown in the publication of a Japanese patient application laid open No. 30331 1981, by utilizing the peculiarity of a living body in an infrared light range, for example, the fact that the variation of the tone is larger in the infrared light range, a color separating filter in a visible light range to an infrared light range is provided on the front surface of a solid state imaging device to make it possible to detect an affected part which has been difficult to sense only in the visible light range.

The infrared light is known to be easy to penetrate within a living body. By observing with an infrared light, such tissue interior as, for example, the blood flow within the vein below the mucous membrane or the minute structure of the vein can be observed.

However, in the above mentioned prior art example, there is a problem that, as the observing wavelength range is fixed, for example, in the case of the observation by utilizing an infrared light, a picture image in the general visible light range will not be obtained and therefore it will be difficult to compare both picture images.

There are also problems that, when a filter in an infrared light range is combined with a color separating filter in a visible light range, the respective pixels of the visible light range picture image and infrared light range picture image will reduce, that is, the resolution will reduce and that, in a frame sequential system wherein a color picture image is obtained by inputting a light of a wavelength range difference in time series, if many filters are provided in a visible light range to an infrared light range, the respective aperture rates will reduce, therefore the light amount will reduce and the sensitivity will reduce.

It is also known that knowing the amount of hemoglobin and the distribution of oxygen saturation degrees in a blood serves to early discover a disease. As a method of determining the amount of hemoglobin and the oxygen saturation degree in a blood, for example, as shown in the publication of a Japanese utility model application laid open No. 151705/1986, there is a method wherein they are determined from picture images in a plurality of specific wavelength ranges related to hemoglobin in the blood.

However, with the camera shown in the above mentioned prior art example, as the observed wavelength range is fixed, generally a color picture image in a visible range can not be obtained and, for example, a special picture image containing an information of a blood and a picture image in a general visible range can not be compared with each other.

By the way, in U.S. Pat. No. 4,717,952, there is disclosed an apparatus whereby a color picture image in a visible range and a picture image in a near infrared range can be observed. However, in this prior art example, the picture image in the near infrared range is a monochromatic picture image by one wavelength range and the amount of hemoglobin and the oxygen saturation degree in a blood can not be thereby known.

OBJECT AND SUMMARY OF THE INVENTION

An object of the present invention is to provide an endoscope apparatus whereby a color picture image in a general visible range and a special picture image by a combination of specific wavelength ranges can be switched and observed without reducing the resolution.

Another object of the present invention is to provide an endoscope apparatus whereby a color picture image in a general visible range can be obtained by a simultaneous system and this color picture image in the visible range and a special picture image by a combination of specific wavelength ranges can be switched and observed without reducing the resolution of this color picture image in the visible range.

Further another object of the present invention is to provide a small endoscope apparatus whereby a plurality of optical characteristic images can be obtained without reducing the resolution.

The endoscope apparatus of the present invention comprises an endoscope body having an elongate insertable part having an observing window in the tip part and an image forming optical system forming an object image by receiving a light returning from the object and entering through the above mentioned observing window, an imaging means imaging the object image formed by the above mentioned image forming optical system, a first wavelength zone separating means separating the object image into images in a plurality of wavelength ranges, a second wavelength zone separating means separating the object image into images in a plurality of wavelength ranges of a combination different from the above mentioned first wavelength range separating means, a signal processing means processing signals for the above mentioned imaging means in response to the respective wavelength ranges separated by the above mentioned first wavelength range separating means or second wavelength range separating means and a switching means switching the above mentioned first wavelength range separating means and second wavelength range separating means. All pixels of the above mentioned imaging means corresponding to the above mentioned second wavelength range separating means are included in all pixels of the above mentioned imaging means corresponding to the above mentioned first wavelength range separating means.

The other features and advantages of the present invention will become apparent enough with the following explanation.

BRIEF DESCRIPTION OF THE DRAWINGS

FIG. 1 is a block diagram showing the formation of an endoscope apparatus.

FIG. 2 is a side view showing the entire endoscope apparatus.

FIG. 3 is an explanatory view showing an example of a layout of color separating filters.

FIG. 4 is an explanatory diagram showing an example of a spectral transmission characteristic of color separating filters.

FIG. 5 is an explanatory diagram showing another example of a spectral transmitting characteristic of color separating filters.

FIG. 6 is an explanatory view showing a rotary filter.

FIG. 7 is an explanatory diagram showing a spectral transmission characteristic of the rotary filter.

FIG. 8 is a block diagram showing the formation of an endoscope apparatus.

FIG. 9 is an explanatory diagram showing a spectral transmission characteristic of color separating filters.

FIG. 10 is an explanatory view showing a rotary filter.

FIG. 11 is an explanatory diagram showing a spectral transmission characteristic of a rotary filter.

FIG. 12 is a block diagram showing the formation of an endoscope apparatus.

FIG. 13 is an explanatory diagram showing a spectral transmission characteristic of color separating filters.

FIG. 14 is an explanatory view showing a rotary filter.

FIG. 15 is an explanatory diagram showing a scattered reflection spectrum of a blood by the difference of the oxygen saturation degree of hemoglobin.

FIG. 16 is an explanatory diagram showing a spectral transmission characteristic of a rotary filter.

FIG. 17 is an explanatory diagram showing another example o spectral transmission characteristic of a rotary filter.

FIG. 18 is an explanatory diagram showing a scattered reflection spectrum of a blood by the difference of the oxygen saturation degree of hemoglobin.

FIG. 19 is an explanatory diagram showing a spectral transmission characteristic of a rotary filter.

FIG. 20 is an explanatory diagram showing another example of a spectral transmission characteristic of a rotary filter.

FIG. 22 (A) is an explanatory view showing the formation of a solid state imaging device.

FIG. 22 (B) is an explanatory view showing an optical filter.

FIG. 22 (C) is an explanatory view showing the optical filter in another state.

FIG. 23 is a block diagram showing the formation of an imaging apparatus.

FIGS. 24 and 25 relate to the seventh embodiment of the present invention.

FIG. 25 (A) is an explanatory view showing a solid state imaging device.

FIG. 25 (B) is an explanatory view showing an optical filter.

FIG. 25 (C) is an explanatory view showing the optical filter in another state.

FIG. 26 (A) is an explanatory view showing a solid state imaging device.

FIG. 26 (B) is an explanatory view showing an optical filter.

FIG. 27 is a block diagram showing the formation of an imaging apparatus.

FIG. 28 (A) is an explanatory view showing a solid state imaging device.

FIG. 28 (B) is an explanatory view showing the position of an optical filter at a time a.

FIG. 28 (C) is an explanatory view showing the position of the optical filter at a time b.

FIG. 28 (D) is an explanatory view showing the position of the optical filter at a time c.

FIGS. 29 to 39 relate to the ninth embodiment of the present invention.

FIG. 29 is an explanatory view showing the formation of an endoscope apparatus.

FIG. 30 is an explanatory view showing a band pass filter turret.

FIG. 31 is an explanatory view showing a color filter array.

FIG. 32 is an explanatory diagram showing transmitted wavelength ranges of the respective filters of the color filter array.

FIGS. 33 and 34 are explanatory views showing the variation of the extinction of a blood by the variation of the oxygen saturation degree of hemoglobin.

FIGS. 35 to 39 are explanatory views showing transmitted wavelength ranges of respective filters of a band pass filter turret.

FIG. 40 is an explanatory diagram showing the formation of an endoscope apparatus.

FIG. 41 is an explanatory diagram showing transmitted wavelength ranges of respective filters of a rotary filter. FIG. 42 is a block diagram showing a processing circuit for determining the amount of hemoglobin and oxygen saturation degree.

DETAILED DESCRIPTION OF PREFERRED EMBODIMENTS

Figure 1:
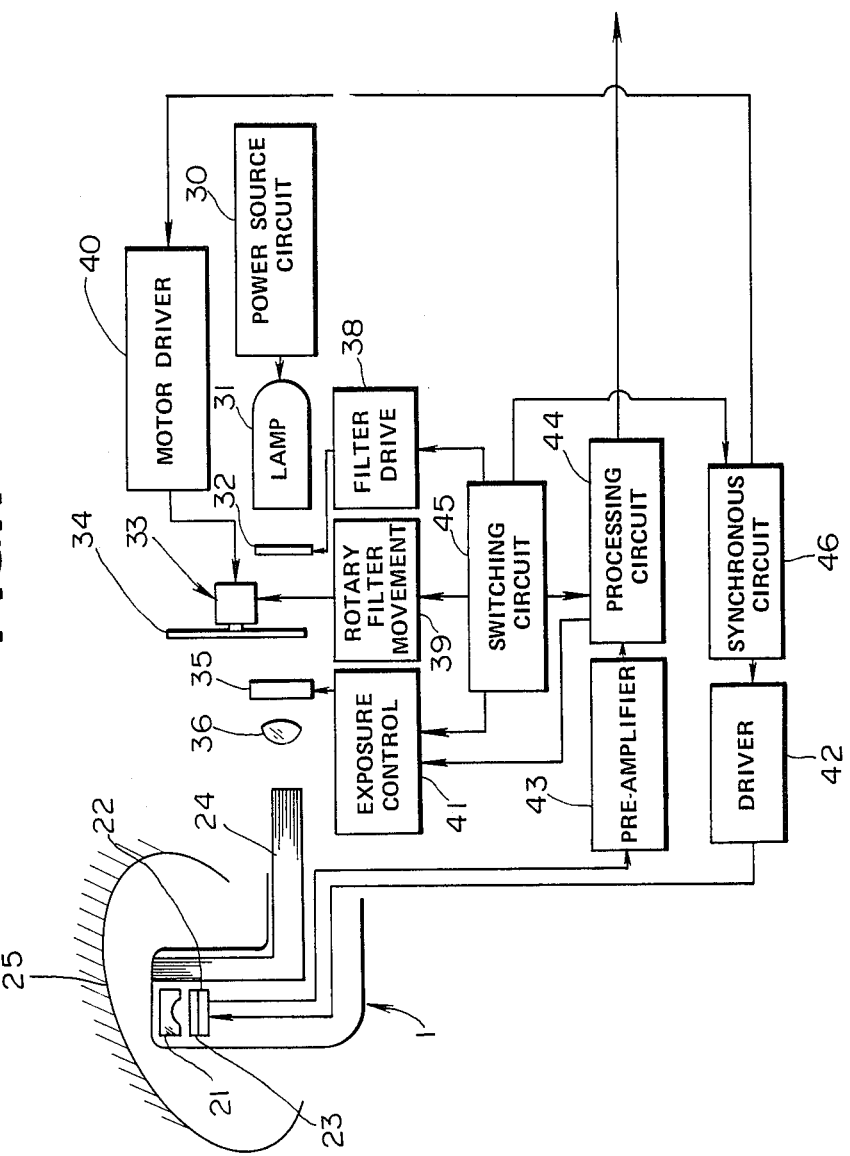
FIGS. 1 to 7 relate to the first embodiment of the present invention.
Figures 2, 3:
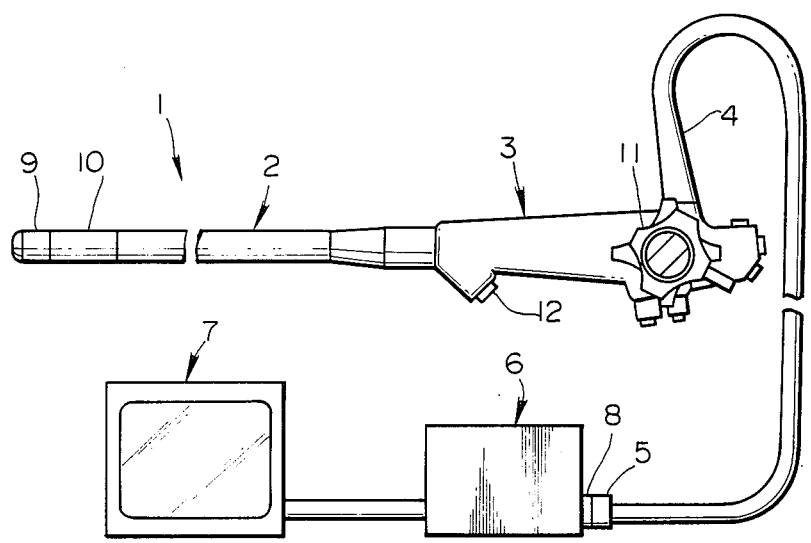

As shown in FIG. 2, an electronic endoscope 1 is provided with an elongate and, for example, flexible insertable part and a thick operating part 3 connected to the rear end of this insertable part. A universal cord 4 is extended sidewise from the rear end part of the above mentioned operating part 3 and is provided at the tip with a connector 5 which is to be connected to a connector receptacle 8 of a video processor 6 containing a light source apparatus and signal processing circuit. A color monitor 7 as a displaying means is to be connected to the above mentioned video processor 6.

The above mentioned insertable part 2 is provided on the tip side with a rigid tip part 9 and a curvable part 10 on the rear side adjacent to this tip part 9 in turn. The above mentioned operating part 3 is provided with a curving operation knob 11 so that, by rotating and operating this curving operation knob 11, the above mentioned curable part 10 may be curved vertically and horizontally. The above mentioned operating part 3 is provided with an inserting port 12 communicating with a treating tool channel provided within the insertable part 2.

The above mentioned tip part 9 is provided with an image forming optical system 21 consisting of an objective lens or the like a solid state imaging device 22 as an imaging means is arranged in the image forming position of this image forming optical system 21. A color separating filter 23 as a first wavelength range separating means is provided on the front surface of this solid state imaging device 22 and is made by mosaic-like arraying color filters transmitting the respective color lights of cyanine (Cy), green (G) and yellow (Y), for example, as shown in FIG. 3. In this embodiment, the respective color filters of the above mentioned color separating filter 23 have such spectral transmission characteristics as transmit not only the respective color lights of cyanine (Cy), green (G) and yellow (Y) but also the light in the infrared wavelength range. By the way, the above mentioned color separating filter 23 is not limited to that shown in FIGS. 3 and 4 but may be a mosaic-like array of color filters transmitting not only the color lights of red (R), green (G) and blue (B) but also the light in the infrared wavelength range as shown, for example, in FIG. 5.

Also, the solid state imaging device 22 has a sensitivity in the wavelength range from the visible light range to the infrared light range and is to be connected to a video signal processing circuit within the above mentioned video processor 6 through a signal line inserted through the above mentioned insertable part 2 and universal cord 4 and connected to the connector 5.

Also, a light guide 24 is inserted through the above mentioned insertable part 2 and universal cord 4, is arranged on the tip surface at the tip of the tip part 9 and is connected in the base end part with the connector 8. An illuminating light from the light source apparatus within the above mentioned video processor 6 will enter the above mentioned light guide 24 on the entrance end surface of the base end part, will be led to the tip part 9 by this light guide 24, will be emitted out of the tip surface and will be radiated to an object 25 to be observed.

The light source apparatus within the above mentioned video processor 6 is provided with a lamp 31 fed with an electric power by a power source circuit 30 and emitting a light in a wavelength range from an observing visible light range to an infrared light range. Between this lamp 31 and the entrance end surface of the above mentioned light guide 24, there are arranged in turn an infrared cutting filter 32 transmitting only the wavelength in the visible light range among the light emitting wavelengths of the lamp 31 and absorbing or reflecting the wavelength in the infrared range, a rotary filter 34 as a second wavelength range separating means rotated and driven by a motor 33, an iris 35 adjusting the amount of the beam within the light path and a lens 36 condensing the beam to enter the above mentioned light guide 24 on the entrance end surface.

Figure 6:
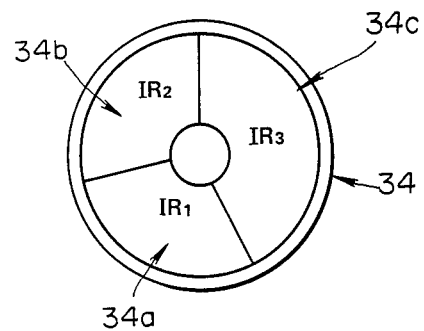
Figure 7:
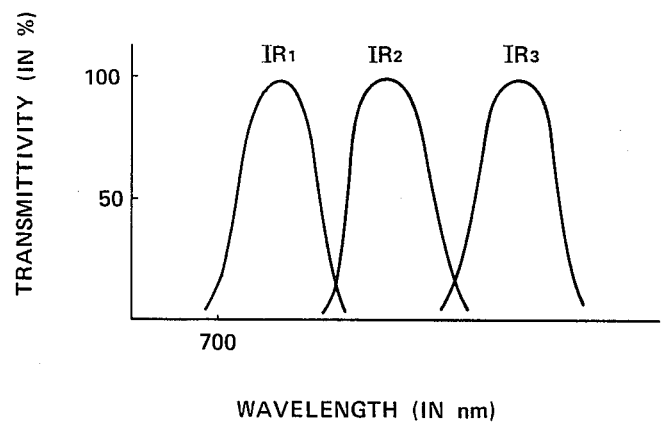
Figure 8:
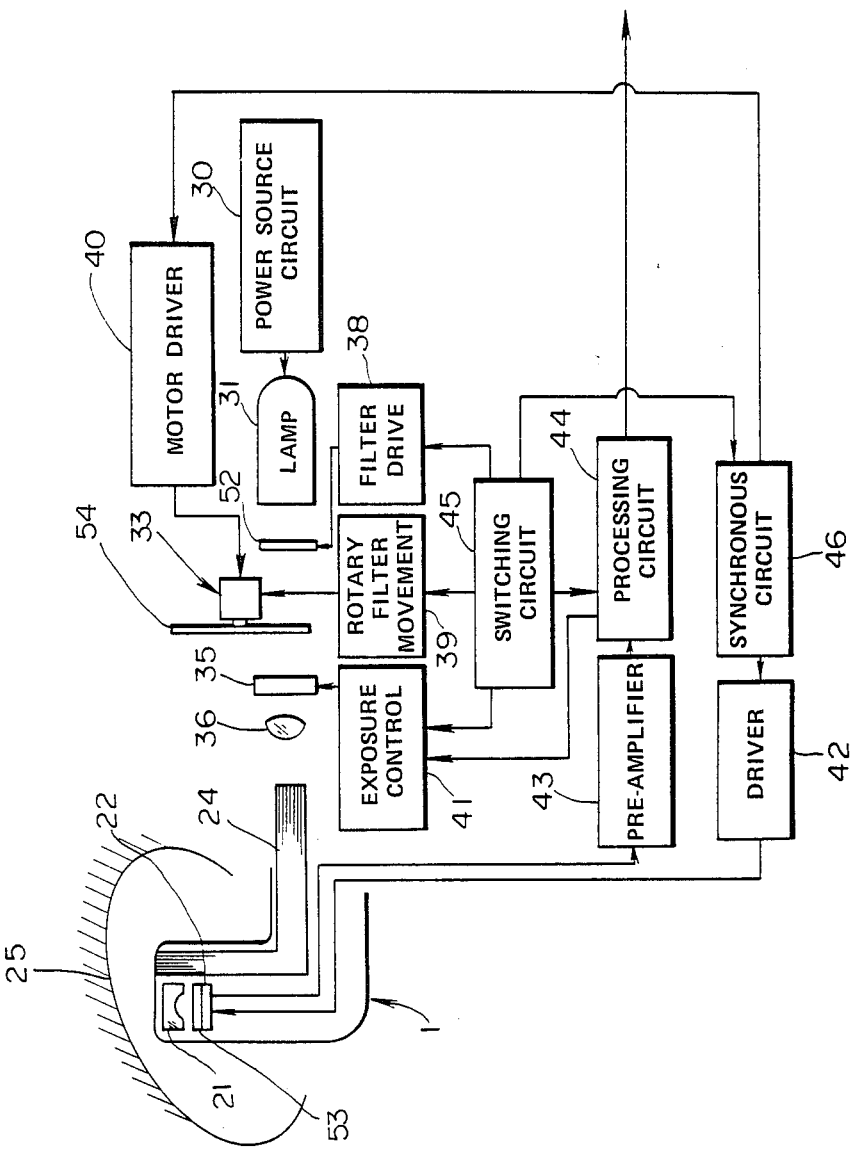
FIGS. 8 to 11 relate to the second embodiment of the present invention.

The above mentioned rotary filter 34 is formed by arraying in the rotating direction as shown in FIG. 6 filters 24a, 34b and 34c transmitting the lights of wavelength ranges IR1, IR2 and IR3 made by dividing an infrared light range into three ranges as shown in FIG. 7.

The above mentioned infrared cutting filter 32 is inserted into and removed from the illuminating light path by an infrared cutting filter driving apparatus 38 and the rotary filter 34 is inserted into and removed from the illuminating light path by a rotary filter moving apparatus 39. The above mentioned motor 33 is driven and controlled by a motor driver 40. The above mentioned iris 35 is controlled by an exposure controlling circuit 41.

On the other hand, the above mentioned solid state imaging device 22 is driven by a driven 42 provided within the video processor 6 and photoelectrically converts an observed object image. The output signal of this solid state imaging device 22 will be amplified by a pre-amplifier 43 and then will be input into a processing circuit 44 provided within the above mentioned video processor 6. By this processing circuit 44, the output signal of the above mentioned solid state imaging device 22 will be processed to have, for example, the white balance, $\gamma$ and matrix corrected and will be converted to a general video signal to be output. Also, in this embodiment, when the above mentioned processing circuit 44 is provided with two circuits corresponding, for example, to respective systems, a signal corresponding to two systems of a simultaneous system in which the observed object is color-separated by the above mentioned color separating filter 23 and a frame sequential system in which the observed object is color-separated by the above mentioned rotary filter 34 will be able to be processed. The video signal from this processing circuit 44 will be input into the color monitor 7 and the observed object image will be color-displayed by this color monitor 7.

A synchronous circuit 46 timing the reading-out and transfer of the solid state imaging device 22 by the driver circuit 42 and generating a synchronous signal of the entire system is provided so that the timing of the above mentioned driver circuit 42 and motor driver 40 may be controlled by this synchronous circuit 46.

The above mentioned two systems are switched by a switching circuit 45 controlling the above mentioned infrared cutting filter driving apparatus 38, rotary filter moving apparatus 39, exposure controlling circuit 41, processing circuit 44 and synchronous circuit 46. In case the simultaneous system is to be used, the infrared cutting filter 32 is interposed in the illuminating light path, the rotary filter 34 is retreated from the illuminating light path, the iris 35 is controlled to be of a proper exposure and the driver circuit 42 and processing circuit 44 are made to correspond to the simultaneous system. On the other hand, in case the field sequential system is to be used, the infrared cutting filter 32 is retreated from the illuminating light path the rotary filter 34 is interposed in the illuminating light path, the iris 35 is controlled to be of a proper exposure and the driver circuit 42 and processing circuit 44 are made to correspond to the field sequential system. By the way, in this case, for example, the respective colors of B, G and R will be allotted to the wavelength ranges IR1, IR2 and IR3 three-divided by the above mentioned rotary filter 34 and the observed object image in the infrared light range will be quasi-color-displayed.

The operation of this embodiment by the above formation shall be explained in the following.

First of all, in case observed object Image in the visible light range is observed, the simultaneous system will be selected by the switching circuit 45, the infrared light cutting filter 32 will be interposed in the illuminating light path and the rotary filter 34 will be retreated from the illuminating light path. The light in the wavelength range from the visible light range to the infrared light range will be emitted from the lamp 31 by the electric power fed from the power source circuit 30 and will have the wavelength in the infrared light range cut by the infrared light cutting filter 32 and only the light in the visible light range will pass through the infrared light cutting filter 32. The light having passed through this infrared light cutting filter 32 will not pass through the rotary filter 34 retreated out of the light path but will enter the iris 35, will be adjusted in the light amount so as to be of a proper exposure, then will be condensed by a lens 36 and will enter the light guide 24. This illuminating light will be emitted from the tip surface of the light guide 34 in the tip part 9 of the endoscope and will be radiated to the observed object 25.

The reflected light from such observed object 25 by the above mentioned illuminating light as, for example, a mucous membrane surface will be transmitted through the color separating filter 23 by the images forming optical system 21 and then will form an image on the solid state imaging device 22. By the way, the above mentioned color separating filter 23 separates colors into general Gy, G and Ye and has a sufficient transmission characteristic in the infrared light range and the solid state imaging device 22 has a sensitivity not only to the visible light range but also to the infrared light range. Therefore, in order to accurately reproduce colors, the infrared light cutting filter 32 is provided on the light source side. Also, an infrared light cutting filter not illustrated may be provided on the front surface of the solid state imaging device so as to be free to insert and remove.

The observed object image having passed through the above mentioned color separating filter and formed on the solid state imaging device 22 will be photoelectrically converted to an electric signal corresponding to the tone and brightness. That is to say, by the switching signal of a switching circuit 45, a synchronous circuit 46 will generate a synchronous signal corresponding to the simultaneous system and, by the timing of this synchronous circuit 46, the respective reading out and transferring operations corresponding to the simultaneous system will be repeated by the driver circuit 42. The video signal photoelectrically converted by the abovementioned solid state imaging device 22 will be amplified by a pre-amplifier 43 and will be input into a processing circuit 44. In this processing circuit 44, the signal will be processed by the simultaneous system conforming to the formation of the color separating filter 23 and the reading out mode and will be output as converted to a video signal observable with a general color monitor 7. The observed object image in the visible light range will be displayed in the color monitor 7.

On the other hand, in case the observed object image in the infrared light range is observed, the frame sequential system will be selected by the switching circuit 45, the infrared cutting filter 32 will be retreated from the illuminating light path and the rotary filter 34 will be interposed in the illuminating light path. The light in the wavelength range from the visible light range to the infrared light range will be emitted from the lamp 31, will not pass through the infrared light cutting filter 32 but will enter the rotary filter 34 and will be made lights in the wavelength ranges IR1, IR2 and IR3 in turn by this rotary filter 34. The lights will enter the iris 35, will be adjusted in the light amount so as to be of a proper exposure, then will be condensed by the lens 36 and will enter the light guide 24. By the way, an exposure controlling circuit 41 will control the iris 35 in advance when a switching signal from the switching circuit 45 is input so that the iris 35 will not unnecessarily move in case the rotary filter 34 is inserted into or removed out of the light path.

The illuminating lights in the wavelength ranges of the above mentioned IR1, IR2 and IR3 will be emitted from the tip surface of the light guide 34 and will be radiated to the observed object 25 in time series. The reflected lights from the observed object 25 by these illuminating lights will pass through the color separating filter 23 and then will be made to form an image on the solid state imaging device 22 by the image forming optical system. Here, as the respective color filters of the color separating filter 23 have sufficient transmission characteristics respectively in the infrared light range and the rotary filter 34 is separated in colors in time series in the infrared light range, the above mentioned color separating filter 23 will not function as a color separating filter. Therefore, optical picture images illuminated by the lights separated in colors in time series by the rotary filter 34 will be formed in turn by the rotary filter 34.

By the switching signal of the switching circuit 45, a synchronous signal corresponding to the frame sequential system will be generated by the synchronous circuit 46. By the timing of this synchronous circuit 46, the solid state imaging device 22 corresponding to the frame sequential system will be read out or transferred by the driver circuit 42. The video signal of this solid state imaging device 22 will be amplified by the pre-amplifier 43 and will be input into the processing circuit 44. In this processing circuit 44, the respective signals corresponding to the IR1, IR2 and IR3 read out in time series are adjusted in the level, then the respective colors, for example, of B, G and R are allotted to the IR1, IR2 and IR3, are synthesized, are converted to a video signal observable with the general color monitor 7 and are output. The observed object image in the infrared light range will be quasi-color-displayed in the color monitor.

Thus, according to this embodiment, as the observed object in the visible light range and infrared light range can be observed, in case the interior of a living body cavity is observed, not only the general endoscope observation by the variation of the concavo-convexes of the mucous membrane surface of the living body and the difference of the tone will be possible by the visible light range but also the observation of the vein running state below the mucous membrane and the disease penetrating range which observation has been impossible in the visible light range will be possible by the infrared light range.

Also, according to this embodiment, two kinds of observation different in the observed wavelength range are possible and the resolution will not reduce as compared with the case of providing filters exclusively for the visible color and for the infrared color for the color separating filter provided on the front surface of the solid state imaging device.

Also, as compared with the case of providing filters for the visible color and for the infrared color in the same manner for the rotary filter, the aperture rate will not vary and which on infrared light cutting filter is used is combined with the system of this embodiment, that is, connected to the video processor 6 of this embodiment, a general visible color picture image and a color picture image in the infrared light range will be able to be observed.

By the way, when the color separating filter 23 is formed by arraying like a mosaic or the like color filters transmitting the respective infrared light therefore the sensitivity will not reduce.

When the color separating filter provided on the front surface of the solid state imaging device of a visible color observing electronic endoscope is made to be of a transmission characteristic of transmitting an infrared light range as in the color separating filter 23 used in this embodiment, when the electronic endoscope usable by a general light source in wavelength ranges the IR1, IR2 and IR3 and transmitting the visible light range and, on the other hand, the rotary filter 34 is made a filter color-separating such visible light ranges as of R. G and B, a color picture image in the infrared light range will be obtained by the simultaneous system and a color picture image in the visible light range will be obtained by the frame sequential system. By the way, in case a color picture image in the infrared light range is obtained by the simultaneous system, the visible light range of the illuminating light will be cut by a visible light cutting filter.

The illumination by the infrared light is not limited to be by the light guide 24 inserted into the body cavity but may be passed through the living body from outside the body. By this passed illumination, as compared with a dropped illumination from within the body cavity, the reflection on the mucous membrane surface will be controlled and therefore the vein running below the mucous membrane and the disease penetrating range will be able to be more definitely observed.

FIGS. 8 to 11 show the second embodiment of the present invention.

Figure 9:
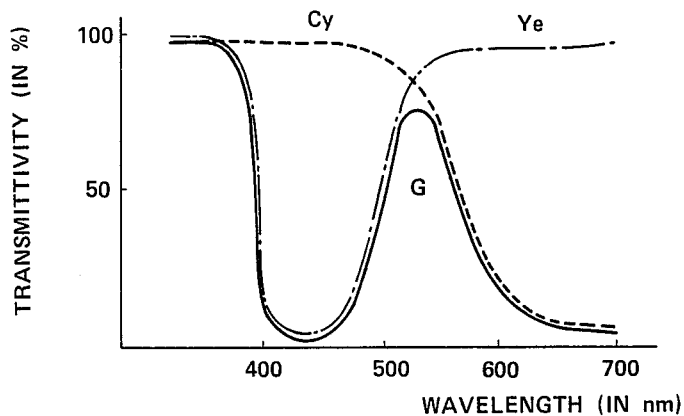
Figure 10:
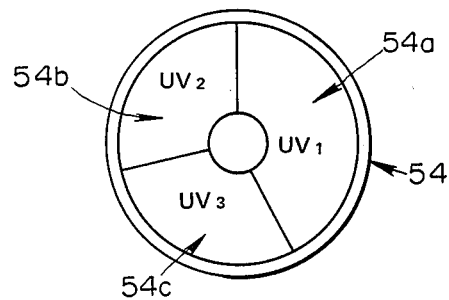
Figure 11:
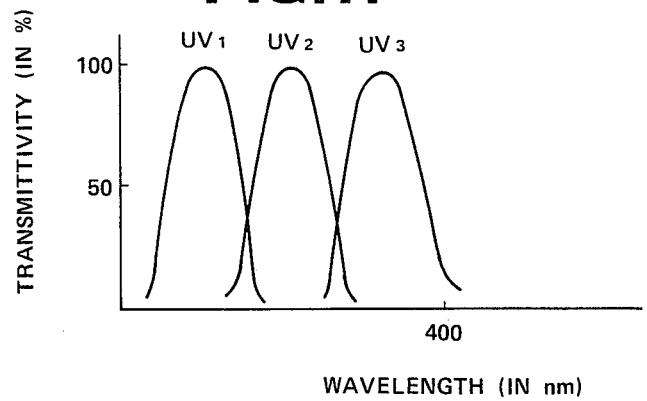
Figure 12:
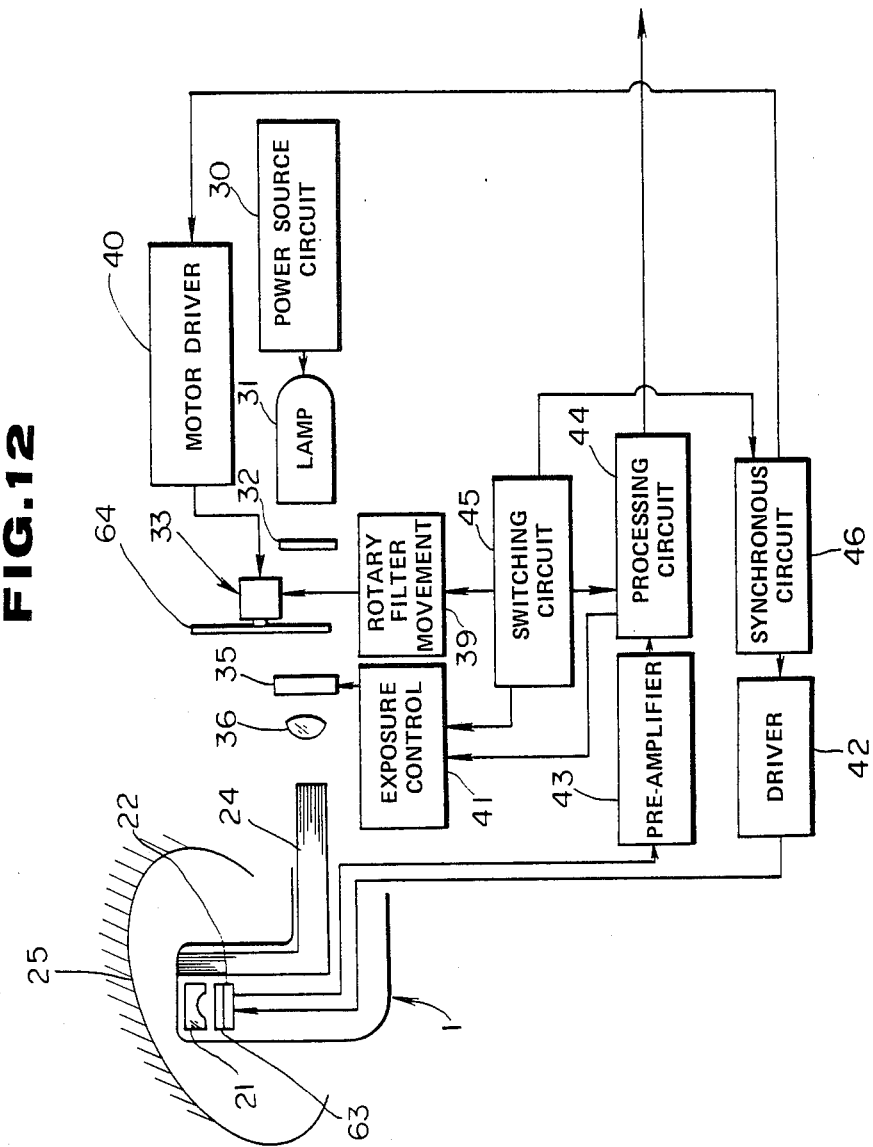
FIGS. 12 to 17 relate to the third embodiment of the present invention.

In this embodiment, instead of the lamp 31 in the first embodiment, a lamp 51 emitting a light in the wavelength range from the ultraviolet light range to the visible light range is provided and, instead of the infrared light cutting filter 32, an ultraviolet light cutting filter 52 is provided. Also, instead of the color separating filter 23, as shown in FIG. 9, a filter 53 separating the color into Cy, G and Ye and having a sufficient transmission characteristic in the ultraviolet light range is provided. Further, instead of the rotary filter 34, as shown in FIG. 11, in a rotary filter 54, filters 54a, 54b and 54c transmitting respectively the lights in the wavelength ranges UV1, UV2 and UV3 made by dividing the ultraviolet light range into three are arrayed in the rotating direction as shown in FIG. 10. The solid state imaging device 22 of this embodiment has a sensitivity in the wavelength range from the visible light range to the ultraviolet light range.

The other formations are the same as in the first embodiment.

In this embodiment, in the case of observing an object to be observed in the visible light range, the simultaneous system will be selected by the switching circuit 45, the ultraviolet light cutting filter will interposed in the illuminating light path and the rotary filter 54 will be retreated from the illuminating light path. By the electric power fed from the power source circuit 30, lights in the wavelength range from the visible light range to the ultraviolet light range will be emitted from the lamp 51, will have the wavelength in the ultraviolet light range cut by the ultraviolet light cutting filter 52, will enter the iris 35 without passing through the rotary filter retreated out of the light path, will enter the iris 35, will have the light amounts adjusted by this iris 35 so that the exposure may be proper, then will be condensed by the lens 36 and will enter the light guide. These illuminating lights will be emitted from the tip surface of the light guide 34 in the tip part 9 of the endoscope 1 inserted into the body cavity and will be radiated to the observed object 25.

The reflected lights from the observed object 25, for example, the mucous membrane surface by the above mentioned illuminating light will be transmitted through the color separating filter 53 by the image forming optical system 21 and then will form an image on the solid state imaging device 221. As the illuminating light is a visible light, the above mentioned color separating filter 53 will function as a color separating filter separating colors into Cy, G and Ye. The color separated optical image will be photoelectrically converted by the solid state imaging device 22 and will be read out as a picture image signal by the driver circuit 42 at a timing synchronized with the synchronous circuit 46. The signal thus read out will be amplified by the preamplifier 43 and then will be processed by the simultaneous system by the processing circuit 44 and will be output as converted to a general video signal. The same as in the first embodiment, the observed object image in the visible light range will be color-displayed in the color monitor 7.

On the other hand, in the case of observing the observed object image in the ultraviolet light range, the field sequential system will be selected by the switching circuit 45, the ultraviolet light cutting filter 52 will be retreated from the illuminating light path and the rotary filter 54 will be interposed in the illuminating light path. Lights in the wavelength range from the visible light range to the ultraviolet light range will be emitted, will enter the rotary filter 54 without passing through the ultraviolet light cutting filter 52 and will be made lights in the wavelength ranges of UV1, UV2 and UV3 in turn by this rotary filter 54. The lights will enter the iris 35, will have the light amounts adjusted so that the exposure may be proper, then will be condensed by the lens 36 and will enter the light guide 24. By the way, the iris 35 will be controlled in advance by the exposure controlling circuit 41 at the time when the switching signal from the switching circuit 45 is input so that the iris 35 may not unnecessarily move in case the rotary filter 54 is inserted into or removed from the light path.

The illuminating lights in the above mentioned wavelength ranges UV1, UV2 and UV3 will be emitted from the tip surface of the light guide 34 and will be radiated to the observed object 25 in time series. The reflected lights from the observed object 25 by these illuminating lights will be transmitted through a color separating filter 53 by the image forming optical system 21 and then will form an image on the solid state imaging device. Here, as the respective color filters of the color separating filter 53 have sufficient transmission characteristic in the ultraviolet light range and the rotary filter 54 separates colors in time series in the ultraviolet light range, the above mentioned color separating filter 53 will not function as a color separating filter. Therefore, optical picture images illuminated by the lights separated in colors in time series by the rotary filter 54 will be formed in turn in the solid state imaging devices 22.

By the switching signal of the switching circuit 45, a synchronous signal corresponding to the frame sequential system will be generated by the synchronous circuit 46 and, at the timing synchronized with this synchronous circuit, the solid state imaging device 22 corresponding to the frame sequential system will be read out by the driver circuit 42. The image signal of this solid state imaging device 22 will be amplified by the pre-amplifier 43 and will be input into the processing circuit 44. In this processing circuit 44, the respective signals corresponding to UV1, UV2 and UV3 and read out in time series will be synthesized by allotting the respective colors, for example, of B, G and R so as to be converted to a video signal observable with the general color monitor 7 and the video signal will be output. Thus, the observed object image in the ultraviolet light range will be quasi-color-displayed in the color monitor 7.

Thus, according to this embodiment, as the observed object image in the visible light range and ultraviolet light range can be observed, the general color picture image by the visible light range and the color picture image in the ultraviolet light range in which minute concavo-convexes on the mucous membrane surface can be observed will be able to be switched and observed without reducing the resolution and sensitivity the same as in the first embodiment.

The other operations and effects are the same as in the first embodiment.

FIGS. 12 to 17 show the third embodiment of the present invention.

Figure 13:
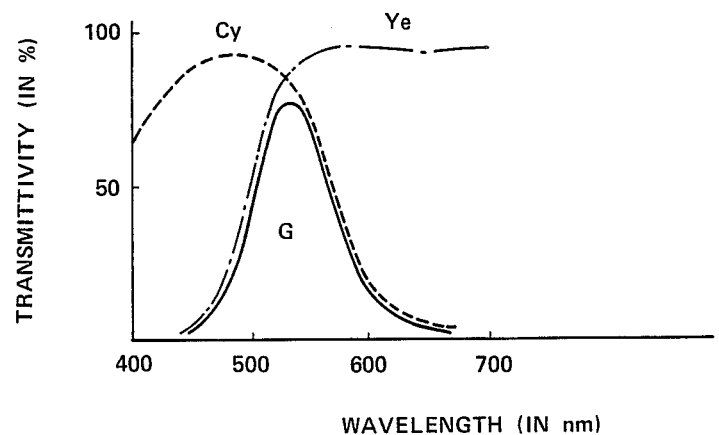
Figure 14:
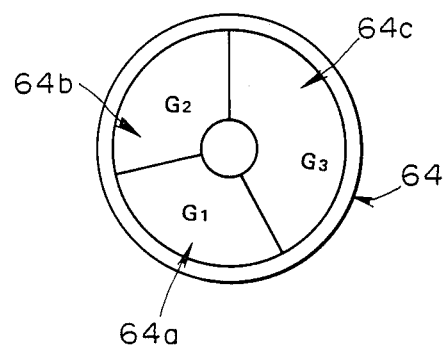
Figure 16:
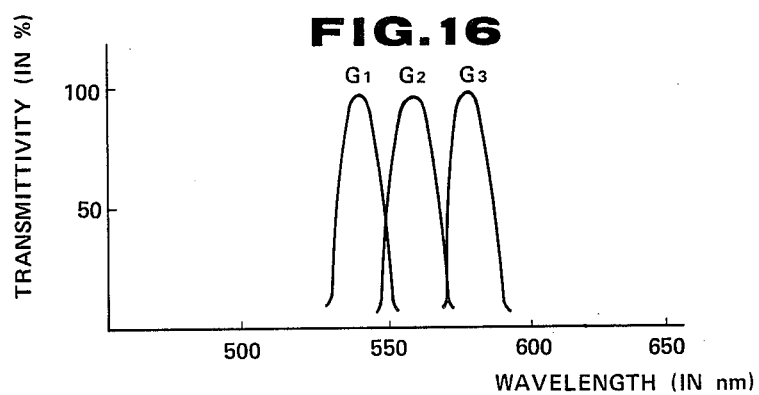

In this embodiment, instead of the color separating filter 23, as shown in FIG. 13, a filter 63 separating colors into Cy, G and Ye is provided. Also, instead of the rotary filter 34, as shown in FIG. 16, there is provided a rotary filter 64 wherein filters 64a, 64b and 64c transmitting lights in wavelength ranges G1, G2 and G3 obtained by dividing the green color light range into three are arrayed in the rotating direction as shown in FIG. 14. The filter driving apparatus 38 is not provided and the infrared light cutting filter 32 in this embodiment is always interposed in the illuminating light path.

Figure 15:
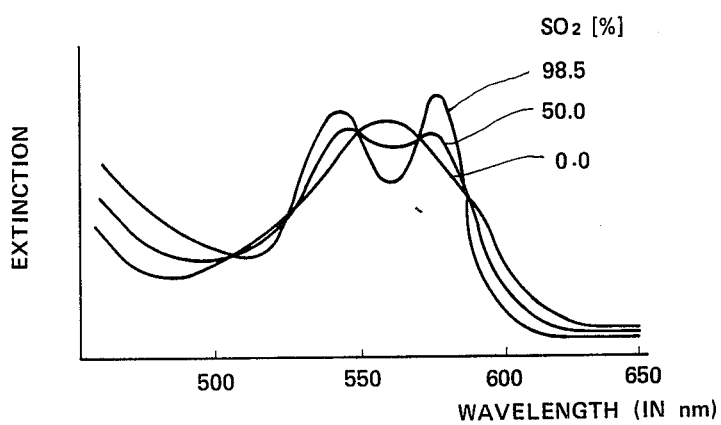

Now, the scattered reflection absorption) spectrum of a blood having a hemoglobin oxygen saturation degree (rate of hemoglobin oxide $SO_2$ to the all amount of hemoglobin), for example, of 0.0, 50.0 or 98.5 (%) will vary as shown in FIG. 15 with the variation of $SO_2$. That is to say, with the reduction of $SO_2$, the two-peak oxidized type hemoglobin pattern will vary to a one-peak reduced type hemoglobin pattern with 569 mm, 586 mm, and the like as equal absorbing points. The respective filters 64a, 64b and 64c of the above mentioned rotary filter 64 will transmit the lights of G1, G2 and G3 from the short wavelength range side in the wavelength range in which the variation of the extinction of the blood is large as shown in FIG. 16.

The other formations are the same as in the first embodiment.

In this embodiment, in the case of observing an observed object image in the visible light range, the simultaneous system will be selected by the switching circuit 45 and the rotary filter 64 will be retreated from the illuminating light path. The light emitted from the lamp 31 will have the wavelength in the infrared light range cut by the infrared light cutting filter 32, will not pass through the rotary filter 64 retreated out of the light path, will enter the iris 35, will have the light amount adjusted by this iris so that the exposure may be proper, will be condensed by the lens 36 and will enter the light guide 24. This illuminating light will be projected out of the tip surface of the light guide 34 of the tip part 9 of the electronic endoscope 1 inserted into the body cavity and will be radiated to the object 25 to the observed.

The light reflected from the observed object 25, for example, the mucous membrane surface by the above mentioned illuminating light will be transmitted through a color separating filter 63 by the image forming optical system 21 and will form an image on the solid state imaging device 22. The optical image having colors separated into Cy, G and Ye by this color separating filter 63 will be photoelectrically converted by the solid state imaging device 22 and will be read out as a video signal by the driver circuit 42 at the timing synchronized with the synchronous circuit 46. The signal thus read out will be amplified by the pre-amplifier 43, then will be processed in the simultaneous system by the processing circuit and will be output as converted to a general video signal and, the same as in the first embodiment, the observed object image in the visible light range will be color-displayed in the color monitor 7.

On the other hand, if the frame sequential system is selected by the switching circuit 45, the rotary filter 64 will be interposed in the illuminating light path. The light from the lamp 31 will pass through the infrared light cutting filter 32, will enter the rotary filter 64 and will be made lights of wavelength ranges G1, G2 and G3 in turn by this rotary filter 64. Then, the lights will enter the iris 35, will have the light amounts adjusted by this iris 35 so that the exposure may be proper, then will be condensed by the lens 36 and will enter the light guide 24. By the way, the iris 35 will be controlled in advance by the exposure controlling circuit 41 at the time when the switching signal from the switching circuit 45 is input so that the iris 35 may not more unnecessarily in case the rotary filter 64 is inserted into or removed from the light path.

The illuminating lights in the above mentioned wavelength ranges G1, G2 and G3 will be emitted out of the tip surface of the light guide 34 and will be radiated to the observed object 25 in time series. The picture image varied in the reflection characteristic by the variation of $SO_2$ by this illuminating light will be transmitted through the color separating filter 63 by the image forming optical system 21 and will be formed on the solid imaging device 22. Here, in case the respective color filters of the color separating filter 63 are of such complementary color type as in shown in FIG. 13, the component of G will be contained in all pixels. Therefore, the video signals of the respective wavelength ranges G1, G2 and G3 will be read out of all pixels in time series.

By the switching signal of the switching circuit 45, a synchronous signal corresponding to the frame sequential system will be generated by the synchronous circuit 46, the solid state imaging device 22 corresponding to the field sequential system will be read out by the driver circuit 42 at the timing synchronized with this synchronous circuit 46. The video signal of this solid state imaging device 22 will be amplified by the pre-amplifier 43 and will be input into the processing circuit 44.

In this processing circuit 44, the respective signals corresponding to G1, G2 and G3 and read out in time series will be synthesized by allotting the respective colors, for example, of B, G and R, will be converted to a video signal observable in the general color monitor 7 and will be output. Thus, the observed object image in the wavelength range large in the variation of the extinction of the blood will be displayed in quasi colors in the color monitor 7. That is to say, the variation of the oxygen saturation degree of the blood will be observed as the tone.

Thus, according to this embodiment, by the general color picture image by the visible light range, the variations of the form and tone in the mucous membrane will be able to be observed and the oxygen saturation degree of the blood on the mucous membrane will be able to be observed as a video image at a high resolution.

Figure 17:
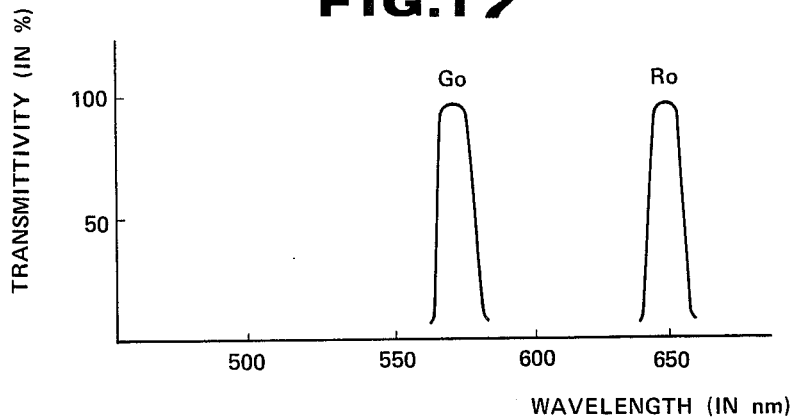

By the way, when filters transmitting the wavelength ranges $G_O$ and $R_O$ having no or little variation of the spectral characteristic of the extinction with the variation of the oxygen saturation degree of the blood as shown in FIG. 17 are provided as respective color filters of the rotary filter and the difference between the wave-length ranges $G_O$ and $R_O$ having no or little variation of such spectral characteristic is made a video image, the blood amount on the mucous membrane surface will be able to be made a video image and the ulcer acting period, curing period and trace period in the ulcer patient will be able to be diagnosed. By the way, in case a color separating filter 63 of such characteristic as is shown in FIG. 13 is used, the observed object image in the above mentioned wavelength ranges $G_O$ and $R_O$ will be able to be obtained from the pixels corresponding to Ye.

Figure 18:
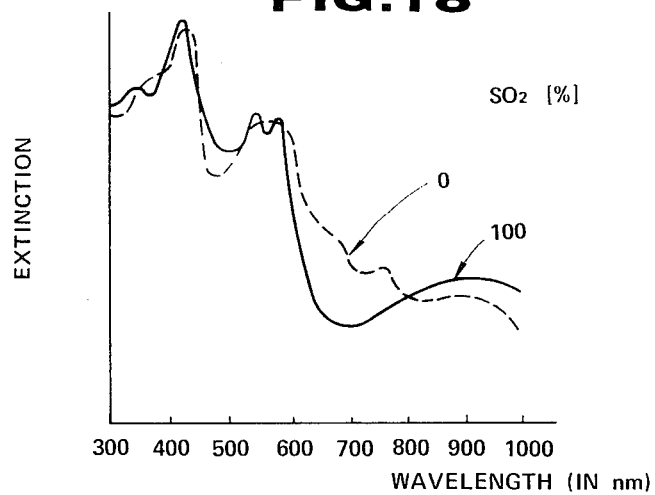
FIGS. 18 to 20 relate to the fourth embodiment of the present invention.
Figure 19:
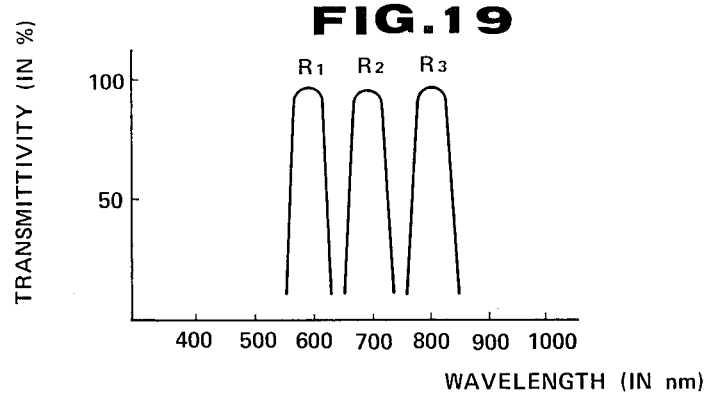
Figure 20:
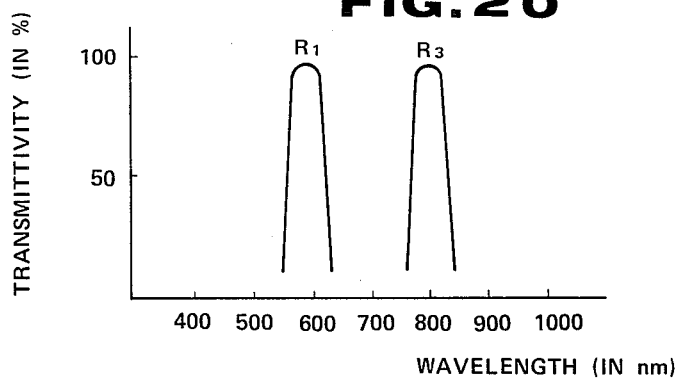

FIGS. 18 to 20 show the fourth embodiment of the present invention.

In this embodiment, as shown in FIG. 18, the respective color filters of the rotary filter 64 in the third embodiment are made filters transmitting the lights of R1, R2 and R3 from the short wavelength range side in the wavelength range large in the variation in response to the variation of the light characteristic with the $SO_2$ variation in the near infrared light range from the visible long wavelength side.

Figure 4:
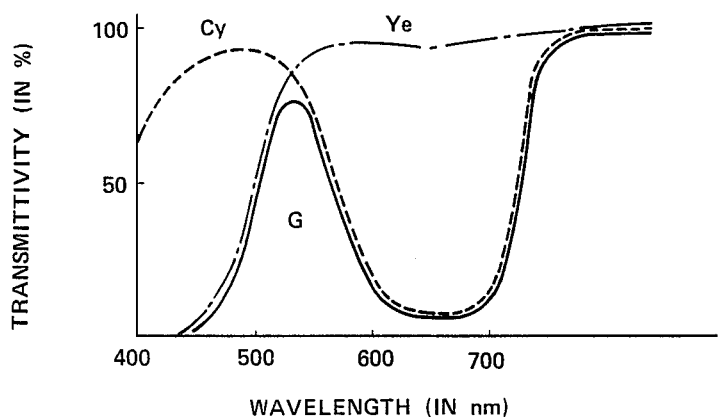
Figure 5:
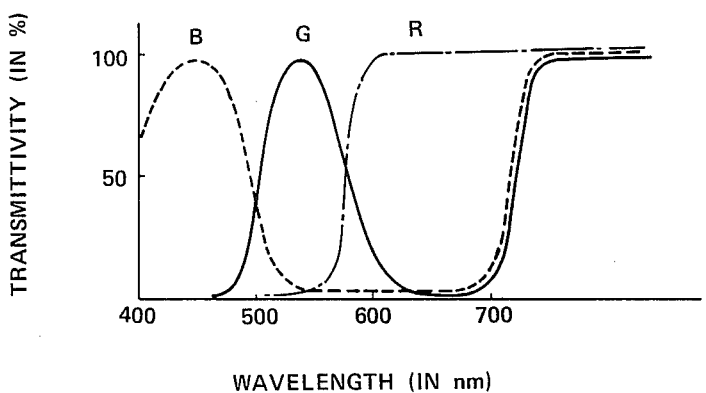

By the way, such color separating filter 23 transmitting also the infrared light range as is shown, for example, in FIG. 4 is used for the color separating filter. Then, the above mentioned observed object images of R1, R2 and R3 will be able to be obtained from the pixels corresponding to Ye.

The other formations, operations and effects are the same as in the third embodiment.

By the way, when filters transmitting the wavelength ranges R1 and R2 having no or little variation of the spectral characteristic of the extinction with the variation of the oxygen saturation degree of the blood as shown in FIG. 20 are provided as respective color filters of the rotary filter and the difference between the wavelength ranges R1 and R3 having no or little variation of such spectral characteristic is made a video image, the blood amount on the mucous membrane surface will be able to be made a video image and the ulcer acting period, curing period and trace period in the ulcer patient will be able to be diagnosed.

By the way, the present invention is not limited to the above mentioned respective embodiments but, for example, the color picture image in the infrared light range or ultraviolet light range may be obtained by the simultaneous system and the color picture image in the visible light range may be obtained by the frame sequential system. In such case, the respective color filters of the rotary filter may be of the primary color system or complementary color system.

When the respective color filters of the color separating filter transmitting Cy, G and Ye in the visible light range and having transmission characteristics in the infrared light range and ultraviolet light range are used and a rotary filter color-separating the infrared light range and a rotary filter color-separating the ultraviolet light range are provided, the visible light range, infrared light range and ultraviolet light range may be selectively observed.

By the way, the imaging means is not limited to the solid state imaging device provided in the tip part of the endoscope but may be a solid state imaging device provided within the operating part or a television camera or the like fitted to or in exchange for the eyepiece part of a fiber scope or the like.

Figure 21:
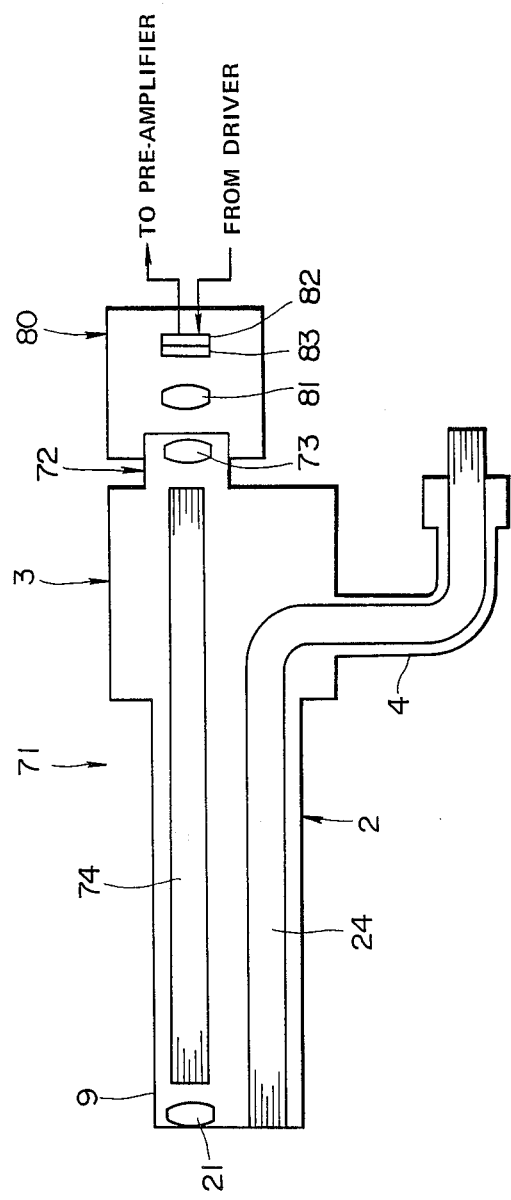
FIG. 21 is an explanatory view showing the formation of an endoscope and externally bitted television camera in the fifth embodiment of the present invention.

FIG. 21 shows the fifth embodiment of the present invention.

In this embodiment, a filter scope and externally fitted television are used instead of the electronic endoscope 1.

A fiber scope 71 is provided with an insertable part 2, an operating part 3 and an eyepiece part 72 provided at the rear end of the operating part 3 and having an eyepiece 73. In the tip part 9 of the above mentioned insertable part 2, instead of the solid state imaging device 22, an image guide 74 consisting of a fiber bundle is arranged with the tip surface in the image forming position of an image forming optical system 21. This image guide 74 is inserted through the insertable part 2 and is opposed on the rear end surface to the above mentioned eyepiece lens 73. The object image formed by the above mentioned image forming optical system 21 will be transmitted to the eyepiece part 72 and will be observed from this eyepiece part 72.

The above mentioned eyepiece part 72 can be removably fitted with an externally fitted television camera 80. This externally fitted television camera 80 has an image forming lens 81 forming an image of the light from the above mentioned eyepiece part 72. A solid state imaging device 82 is arranged in the image forming position of this image forming lens 81. A color separating filter 83 is provided on the front surface of this solid state imaging device 82. This color separating filter 83 is the same as the color separating filter 23 in the first embodiment, the color separating filter 53 in the second embodiment and the color separating filter 63 in the third embodiment. The above mentioned solid state imaging device 82 is to be connected to a driver 42 and pre-amplifier 43.

The other formations, operations and effects are the same as in the first, second, third or fourth embodiment.

As explained above, according to the first to fifth embodiments, there is an effect that observed object images in different wavelength ranges can be observed without reducing the resolution and sensitivity. For example, there are effects that, when a color picture image in the general visible light range and a quasi-color picture image by the observed wavelength range effective to detect the disease part, oxygen saturation degree of the vein and vein running below the mucous membrane are switched and compared with each other, the information of the tissue so far difficult to detect with only the conventional color picture image will be able to be obtained and the diagnosability of the disease part will be able to be elevated.

Figures 22A, 22B, 22C:
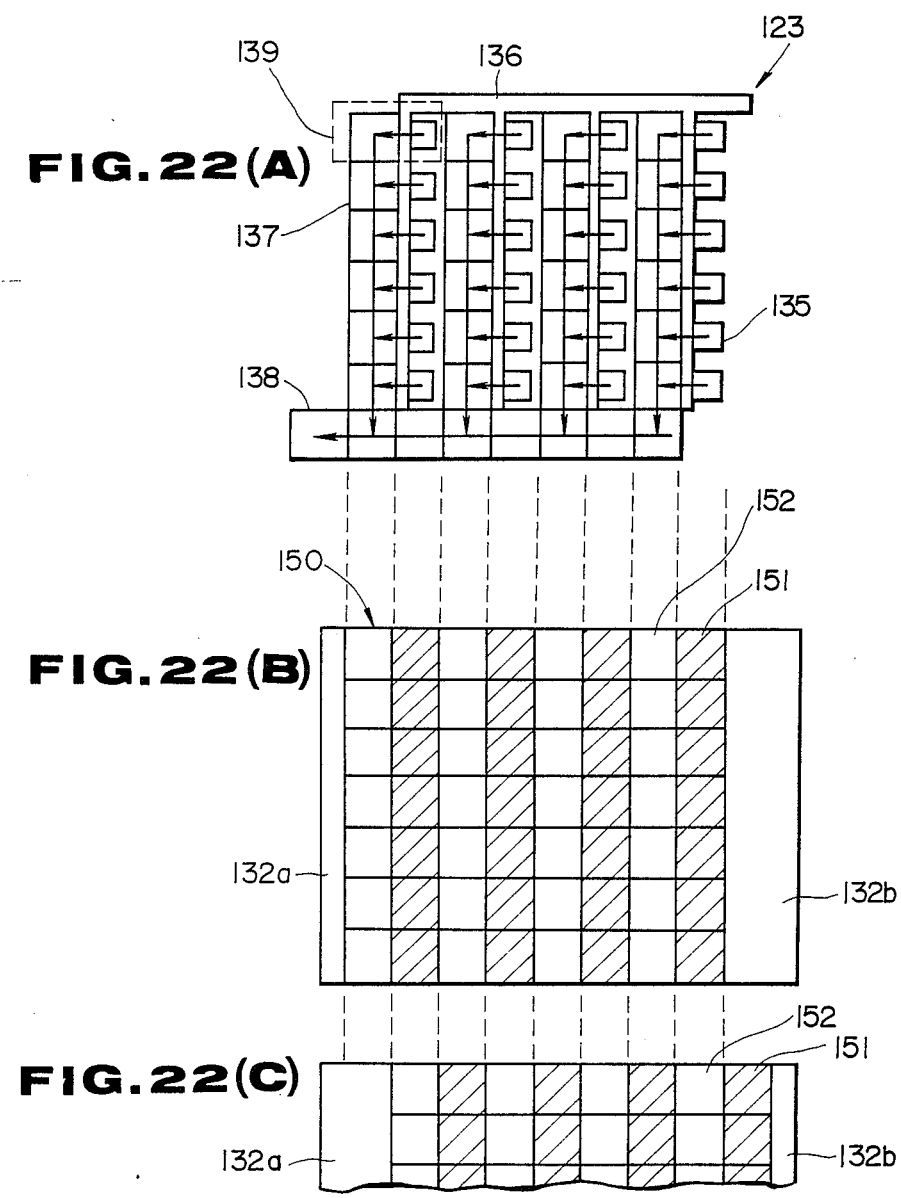
FIGS. 22 and 23 relate to the sixth embodiment of the present invention.
Figure 23:
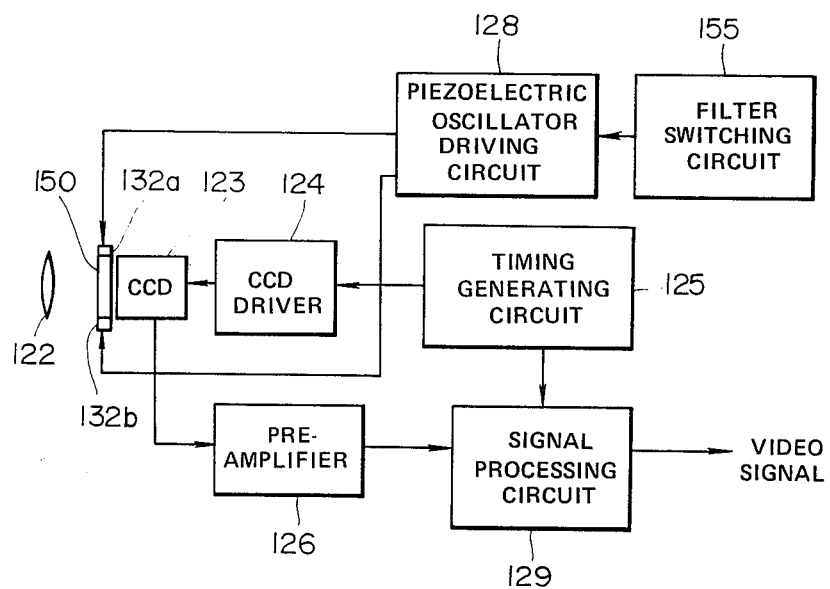

FIGS. 22 and 23 show the sixth embodiment of the present invention.

The appearance of the endoscope apparatus of this embodiment is the same as is shown in FIG. 2.

In this embodiment, as shown in FIG. 23, in the tip part 9, an image forming optical system 122 consisting of an objective lens is provided and, in the image forming position of this image forming optical system 122, a solid state imaging device as an imaging means, for example, a CCD 123 is arranged vertically to the axial direction, for example, of the insertable part. On the front surface side of the above mentioned CCD 123, an optical filter 150 is arranged and piezoelectric oscillators 132a and 132b as moving means moving this optical filter 150 in the diametral direction, that is, in the direction vertical to the optical axis of the image forming optical system 122 are fitted to both end parts in the diametral direction of this optical filter 150.

On the other hand, a CCD driver 124 driving the above mentioned CCD 123 and reading out the signal charge photoelectrically converted and accumulated in the light sensing part is provided within a video processor 6. The driving pulse from this CCD driver 124 will be applied to the above mentioned CCD 123 through a universal cord 4 of the electronic endoscope 1 connected to the video processor 6 and a signal line not illustrated inserted through the insertable part 2. The signal read out of the above mentioned CCD 123 will be amplified by a pre-amplifier 126 provided, for example, within the tip part 9 of the above mentioned electronic endoscope 1, will be input into a signal processing circuit 129 provided within the video processor 6 through a signal line not illustrated inserted through the above mentioned insertable part 2 and universal cord 4 and will be processed by this signal processing circuit 129 so as to be a video signal. The video signal output from this signal processing circuit 129 will be input into a color monitor 7 and an object image will be displayed in this color monitor 7. By the way, the above mentioned timing generating circuit 125 will apply a timing signal also to the above mentioned signal processing circuit 129 to control the timing of this signal processing circuit 129.

Now, as shown in FIG. 22 (A), for example, an interline transfer type CCD is used for the above mentioned CCD 123 and is formed of photosensitive parts 135 converting an optical energy to an electric energy, a reading-out gate 136 reading out the signal charge accumulated in these photosensitive parts, vertically transferring CCD's 137 arranged in the horizontal direction alternately with the above mentioned photosensitive parts 135 and transferring in the vertical direction the signal charge read out of the above mentioned reading-out gate and horizontally transferring CCD's 138 provided below the above mentioned light sensing parts 135 and vertically transferring CCD's 137 and transferring in the horizontal direction the signal charge transferred in the vertical direction by the above mentioned vertically transferring CCD's 137. By the way, in the drawing, the reference numeral 139 represents one pixel including a non-photosensitive part, that is, the vertically transferring CCD 137.

On the other hand, as shown in FIG. 22 (B), the above mentioned optical filter 150 is formed of first filter groups 151 and second filter groups 152 arranged alternately in the positions corresponding to the photosensitive parts 135 of the above mentioned CCD 123 and the positions corresponding to the vertically transferring CCD's 137 which are non-photosensitive parts and different from each other in the optical characteristics.

In this embodiment, the above mentioned first filter groups 151 are mosaic filters for obtaining a general visible color picture image. On the other hand, the above mentioned second filter groups 152 are mosaic filters having transmitted wavelength ranges in the ultraviolet or infrared invisible ranges, that is, filters arranged like a mosaic and having transmission characteristics in the wavelength ranges different from each other within the infrared range or ultraviolet range.

The above mentioned piezoelectric oscillators 132a and 132b are fitted to both end parts in the horizontal direction of the above mentioned optical filter 150, are driven by a piezoelectric oscillator driving circuit 128 and can move the above mentioned optical filter 150 parallelly in the horizontal direction in FIG. 22, for example, when one contracts in the diametral direction and the other extends.

The above mentioned piezoelectric oscillator driving circuit 128 will be controlled by a filter switching circuit 155 and the above mentioned optical filter 150 will be selectively arranged in response to the switching signal of the filter switching circuit 155 so that the first filter group 151 may be arranged on the photosensitive parts 135 as shown in FIG. 22 (B) and that the second filter group 152 may be arranged on the photosensitive parts 135 as shown in FIG. 22 (C).

In this embodiment, when the first filter group 151 for visible color lights is arranged on the photosensitive parts 135 of the CCD 123, a general visible color picture image will be able to be obtained. On the other hand, when the second filter group 152 for invisible lights is arranged on the above mentioned photosensitive part 135, respective colors, for example, of red, green and blue will be allotted respectively to the pixel signals of the respective pixels of the CCD 123 and an image in the invisible range will be displayed in quasi-colors. For example, if filters having a transmitted wavelength range in the infrared light range are used for the above mentioned second filter group 152, an image in the infrared light range will be obtained, the tone difference in the respective parts difficult to distinguish in an image in the general visible light range will be able to be detected from the image in this infrared light range and the information on the vein running state below the mucous membrane and the penetrating range of a tumor will be able to be obtained.

Thus, according to this embodiment, when the optical filter 150 is moved to selectively arrange the first filter group 151 and second filter group 152 on the photosensitive parts 135 of the CCD 123, the visible picture image and invisible picture image (special picture image) will be able to be switched and observed.

Also, when the above mentioned optical filter 150 is continuously moved to vary the rates of the first filter group 151 and the second filter group 152 on the photosensitive parts 135, a picture image in which the general visible picture image and invisible picture image are mixed at any rates will be able to be obtained and the feature of the observed object which has not been able to be observed in the general picture image will be able to be observed.

When a small optical filter 150 or the like of substantially the same shape as of the chip of the CCD 123 is added, a small imaging apparatus whereby a visible picture image and invisible picture image can be observed without reducing the resolution will be able to be formed.

By the way, the spectral characteristic of the above mentioned first filter group 151 and second filter group 152 can be properly selected. For example, the first filter group 151 may be made an infrared light transmitting filter and the second filter group 152 may be made an ultraviolet light transmitting filter. Also, the optical filter may be formed of a visible light transmitting filter group, infrared light transmitting filter group and ultraviolet light transmitting filter group so that, when this optical filter is moved to a position in which the respective filter groups are selectively arranged on the photosensitive parts 135, a visible picture image, infrared light picture image and ultraviolet light picture image will be selectively obtained.

The infrared light transmitting filter and ultraviolet light transmitting filter may not be made mosaic filters but may have only one kind of transmitted wavelength range and the infrared light picture image and ultraviolet light picture image may be displayed as black and white picture images.

By the way, as a combination of the transmitted wavelength ranges of the respective filters in the filter group for special picture images and as the same combination as of the rotary filters in the third or fourth embodiment, the oxygen saturation degree of the blood and the blood amount may be observed.

By the way, as in the sixth embodiment, by moving the optical filter arranged on the front surface side of the CCD 123, the color picture image in the visible range and the special picture image can be switched with each other and, as in the following seventh and eighth embodiments, a plurality of optical characteristic images can be obtained.

FIGS. 24 and 25 show the seventh embodiment of the present invention.

As shown in FIG. 25, the same as in the sixth embodiment, an optical filter 131 formed of a first filter group 141 and second filter group 142 is arranged on the front surface side of the CCD 123. In this embodiment, the above mentioned first filter group 141 is a mosaic filter in which respective color lights of red, green and blue for visible colors are arranged like a mosaic. On the other hand, the above mentioned second filter group 142 is formed of light intercepting members.

As shown in FIG. 24, the output of the pre-amplifier 126 will be input into a signal level detecting circuit 127 provided within the video processor 6 so that the signal level may be detected by this signal level detecting circuit 127. The signal level signal output from this signal level detecting circuit 127 will be input into a piezoelectric oscillator driving circuit 128 driving the above mentioned piezoelectric oscillators 132a and 132b so that the thickness, for example, in the diametral direction may vary. The above mentioned piezoelectric oscillators 132a and 132b will be driven by the above mentioned piezoelectric oscillator driving circuit 128 in response to the signal level detected by the above mentioned signal level detecting circuit 127 to move the above mentioned optical filter 13 in the diametral direction by the amount corresponding to the above mentioned signal level. The output signal of the CCD 123 output through the above mentioned signal level detecting circuit 127 will be input into the signal processing circuit 129 and will be processed by this signal processing circuit 129 so as to be a video signal. The video signal output from this signal processing circuit 129 will be input into the color monitor 7 in which the object image will be displayed.

The same as in the sixth embodiment, the piezoelectric oscillators 132a and 132b are fitted to both end parts in the horizontal direction of the above mentioned optical filter 131, is driven by the above mentioned piezoelectric oscillator driving circuit 128 and can parallelly move the above mentioned optical filter 131 in the horizontal direction. This optical filter 131 will be arranged in any position from the state that the first filter group 141 which is a mosaic filter is arranged on the photosensitive parts 135 in response to the signal level detected by the above mentioned signal level detecting circuit 127 as shown in FIG. 25 (B) to the state that the second filter group 142 consisting of light intercepting members is arranged on the photosensitive parts 135. An iris mechanism is formed of this optical filter, 131, etc. That is to say, in case the light amount entering the above mentioned photosensitive parts 135 is large, the rate of the second filter group 142 arranged on the photosensitive parts 135 will increase but the light amount entering the photosensitive parts 135 will decrease. On the other hand, in case the light amount entering the above mentioned photosensitive parts 135 is small, the rate of the second filter group 142 arranged on the photosensitive parts 135 will decrease but the light amount entering the photosensitive parts 135 will increase.

Thus, in this embodiment, the optical filter 131 formed of the first filter group 141 consisting of mosaic filters arranged alternately in the positions corresponding to the photosensitive parts 135 and the positions corresponding to the vertically transferring CCD's 137 which are non-photosensitive parts and the second filter group 142 consisting of the light intercepting members is arranged on the front surface of the CCD 132. This optical filter 131 will be moved by the piezoelectric oscillators 132a and 132b in response to the signal level detected by the signal level detecting circuit 127. The rates of the first filter group 141 and second filter group 142 arranged on the above mentioned photosensitive part 135 will vary in response to the light amount entering the photosensitive parts 135. That is to say, in case the light amount entering the above mentioned photosensitive parts 135 is large, the rate of the second filter group 142 arranged on the photosensitive parts 135 will increase but the light amount entering the photosensitive parts 135 will decrease. On the other hand, in case the light amount entering the above mentioned photosensitive parts 135 is small, the rate of the second filter group 142 arranged on the photosensitive part 135 will decrease but the light amount entering the photosensitive parts 135 will increase.

Thus, according to this embodiment, a small iris mechanism substantially of the same shape as of the chip of the CCD 123 can be formed of the above mentioned optical filter 131 and the like.

Conventionally, the optical filter positioned on the non-photosensitive parts had no meaning for the signal read out of the CCD 123 but, as in the present invention, when optical characteristics different from each other are given to the optical member positioned on the photosensitive parts and the optical member positioned on the non-photosensitive parts and these optical members are moved, an image (in this embodiment, the image when the entering light amount is varied) of a plurality of optical characteristics will be able to be obtained without making the imaging apparatus large.

By the way, according to this embodiment, as the aperture rate of the pixels varies, an iris mechanism in which the imaged field depth does not vary can be provided and the ND filter becomes unnecessary.

By the way, when the above mentioned optical filter 131 is not continuously moved but is moved so as to be switched to the position shown in FIG. 25 (B) and the position shown in FIG. 25 (C), such operation as of a shutter will be able to be made.

By the simultaneous use of the conventional iris mechanism, the exposure controlling range can be expanded.

Figure 26A:
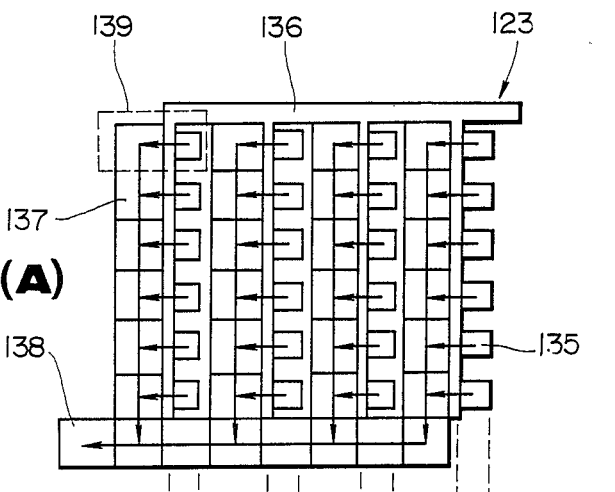
FIGS. 26 to 28 relate to the eighth embodiment of the present invention.
Figure 26B:
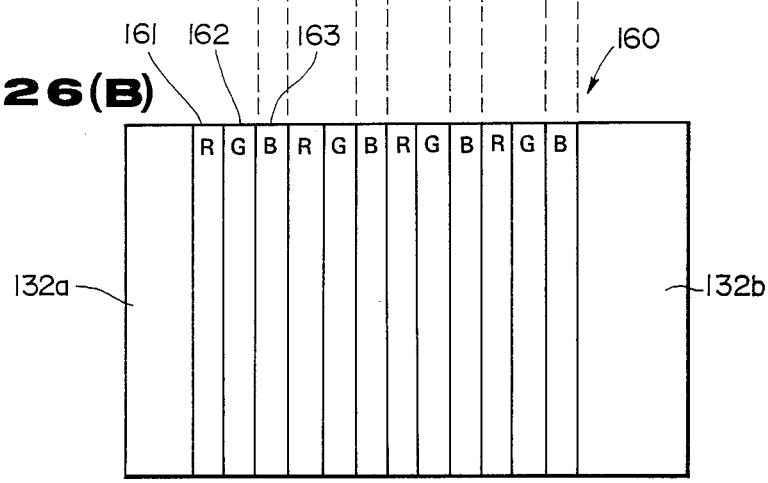
Figure 27:
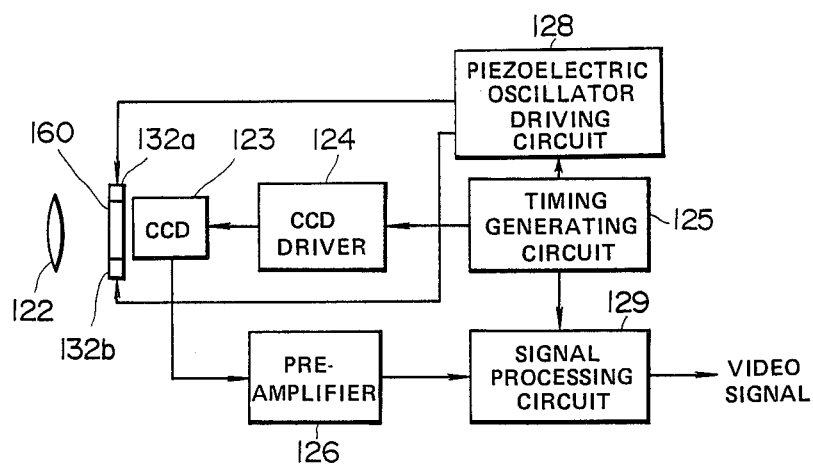
Figure 28A:
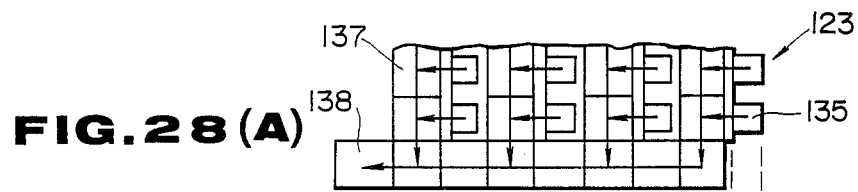
Figure 28A:
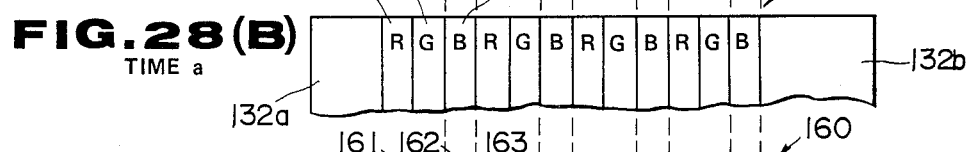
Figure 28A:
Figure 28A:
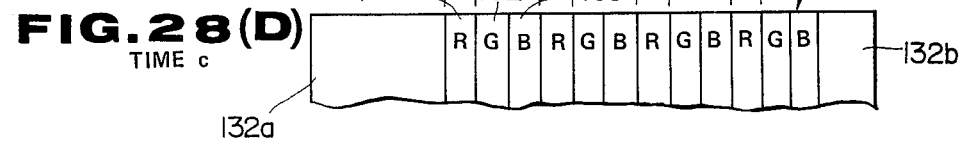

FIGS. 26 to 28 show the eighth embodiment of the present invention.

In this embodiment, as shown in FIG. 26, an optical filter 160 in which a stripe-like R filter 161, G filter 162 and B filter 163 transmitting respectively color lights of red, green and blue are arranged in the horizontal direction in turn within the range in the horizontal direction corresponding to one pixel 139 is arranged on the front surface side of the CCD 123. As shown in FIG. 27, this optical filter 160 can be parallelly moved in the diametral direction (horizontal direction) by the piezoelectric oscillators 132a and 132b driven by the piezoelectric oscillator driving circuit 128. In this embodiment, the above mentioned piezoelectric oscillator driving circuit 128 is controlled by a timing signal from the timing generating circuit 125 applying R. G and B reading out pulses to the CCD 123 so that the above mentioned optical filter 160 will be selectively arranged in the three states of the state that the B filter 163 is arranged on the photosensitive part 135 as shown in FIG. 28 (B), the state that the G filter 162 is arranged on the photosensitive part 135 as shown in FIG. 28 (C) and the state that the R filter 161 is arranged on the photosensitive part 135 as shown in FIG. 28 (D).

In this embodiment, a timing dividing one frame period time into three of a, b and c is generated by the above mentioned timing generating circuit 125 and the piezoelectric oscillator driving circuit 128 drives the piezoelectric oscillators 132a and 132b as synchronized with the respective timings so that the B filter 163 will be arranged on the photosensitive parts 135 at the time of the time a as shown in FIG. 28 (B), the G filter 162 will be arranged on the photosensitive parts 135 at the time of the time b as shown in FIG. 28 (C) and the R filter 161 will be arranged on the photosensitive parts 135 at the time of the time c as shown in FIG. 28 (D).

The above mentioned CCD 123 will be read out as synchronized with the switching of the position of the above mentioned optical filter 160 and picture image signals of R, G and B will be output from this CCD 123 during one frame period.

These picture image signals will be amplified by the pre-amplifier 126 and then will be processed by the signal processing circuit 129 so as to be video signals and R, G and B signals or, for example, a video signal of the NTSC system will be output from this signal processing circuit 129.

Thus, according to this embodiment, a frame sequential system color imaging is made possible by using a general white color light without emitting frame sequential illuminating lights of R, G and B on the light source side.

As such large component parts as the rotating filter and motor are not necessary on the light source side, the entire imaging apparatus can be made small in the size.

By the way, the above mentioned optical filter 160 may not be of a type of such primary colors as R, G and B but may be of a type of such complementary colors as yellow (Ye), magenta (M) and cyanine (Cy).

Also, the position of the above mentioned optical filter 160 may be switched not during one frame period but during one field period.

By the way, in the sixth to eighth embodiments, such element wide in the movable range as a bimorph piezoelectric element may be used for the moving means. Not the optical filter but such solid state imaging device as a CCD may be moved.

The solid state imaging device is not limited to the interline transfer type CCD but an optical filter having a plurality of sets of optical members arrangeable in the positions corresponding to the photosensitive parts and the positions corresponding to the accumulating parts may be provided by using, for example, a frame transfer type CCD. It is needless to say hat further an MOS type imaging device, CDD and CSD will also do.

By the way, in the sixth and seventh embodiments, the color imaging system is not limited to the simultaneous system using a mosaic filter but may be a frame sequential system.

Also, the plurality of sets of optical members of the optical filter are not limited to the combination in the sixth to eighth embodiment but, for example, one set may be of infrared light cutting filters or may be of filters different from each other in the refractive index so that the focal distance may be variable.

By the way, the sixth to eighth embodiment can be applied not only to the electronic endoscope but also to such various imaging apparatus as video cameras.

As explained above, according to the sixth to eighth embodiments, as the optical characteristic of the object image entering the photosensitive parts of the above mentioned solid state imaging device can be varied by varying the relative optical positions of the optical filter having a plurality of sets different from each other in the optical characteristic and the photosensitive parts of the solid state imaging device, there is an effect that an image of a plurality of optical characteristics can be obtained with a small imaging apparatus.

FIGS. 29 to 39 show the ninth embodiment of the present invention.

The appearance of the endoscope apparatus of this embodiment is the same as is shown in FIG. 2.

Figure 29:
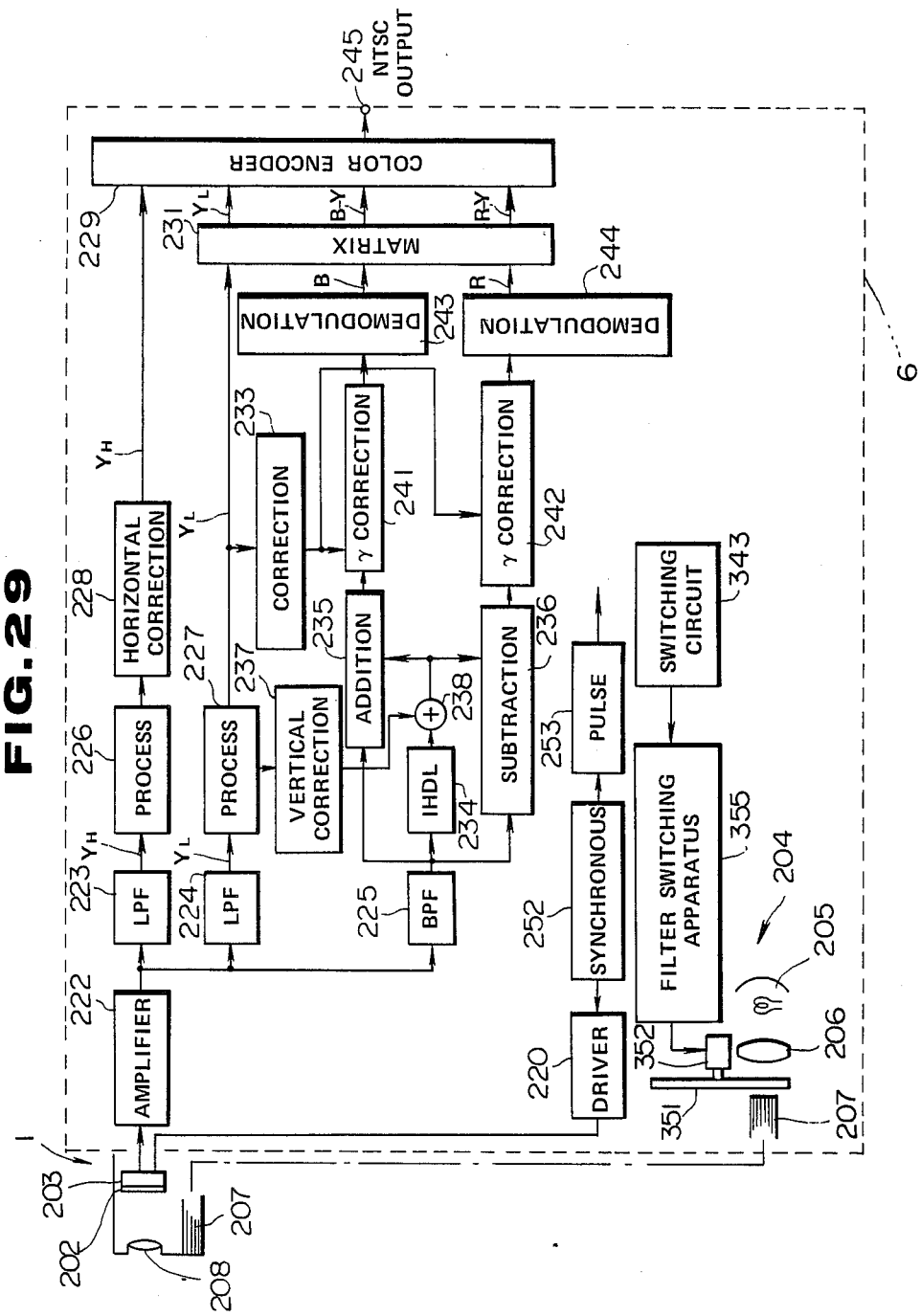

In this embodiment, as shown in FIG. 29, an electronic endoscope 1 has an objective lens system 208 in the tip part of an insertable part and a solid state imaging device 203 provided on the front surface with a color filter array 202 is arranged in the image forming position of this objective lens system 208.

As shown in FIG. 31, the above mentioned color filter array 202 is formed by arranging in the form of a mosaic filters transmitting the lights in the respective wavelength ranges of green (G), cyanine (Cy) and yellow (Ye). Also, as shown in FIG. 32, in this embodiment, the filter transmitting Cy has a characteristic of transmitting also the wavelength range Cy' near 800 nm. in the infrared band and the filter transmitting G has a characteristic of transmitting also the wavelength range G' above about 900 nm. in the infrared band.

A light source part 204 contained in the video processor 6 has a lamp 205 emitting the light in a wide band from the ultraviolet light to the infrared light. The light emitted from this lamp 205 will be condensed by a lens 206 and will enter a light guide 207 at the entrance end.

In this embodiment, a band pass filter turret 351 is arranged between the above mentioned lens 206 and the entrance end of the light guide 207. In this band pass filter turret 351, as shown in FIG. 30, five kinds of filters 351a, 351b, 351c, 351d and 351e having respectively different band pass characteristics are arranged in the peripheral direction. The transmitting characteristics of the respective filters 351a to 351e are shown in FIGS. 35 to 39.

Figure 35:
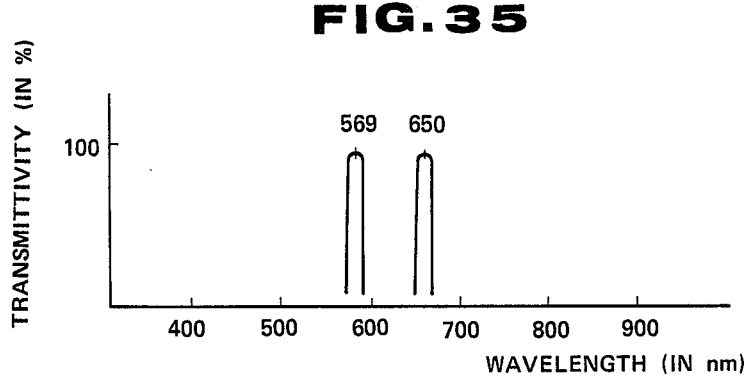
Figure 36:
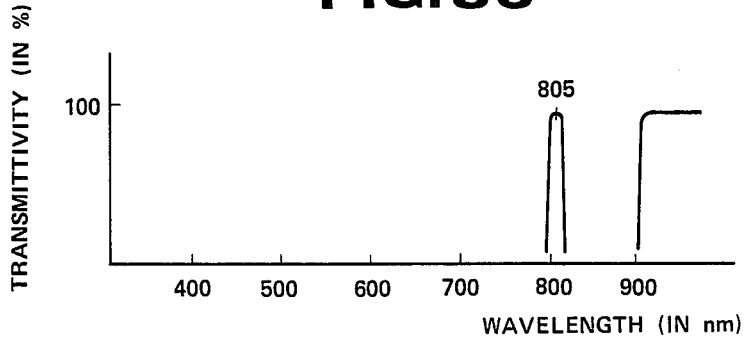
Figure 37:
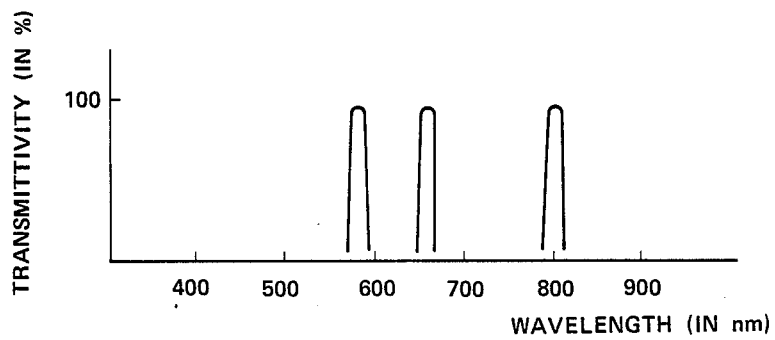
Figure 38:
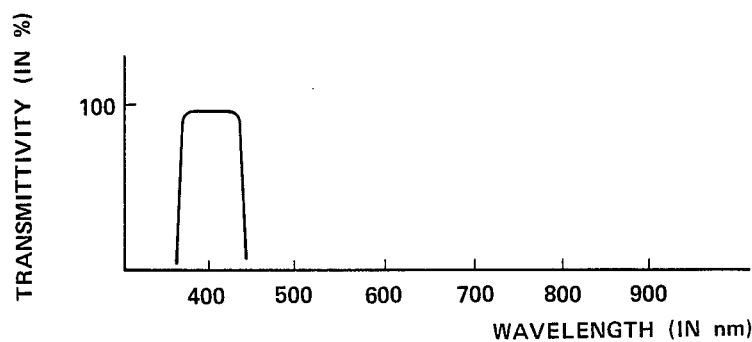
Figure 39:
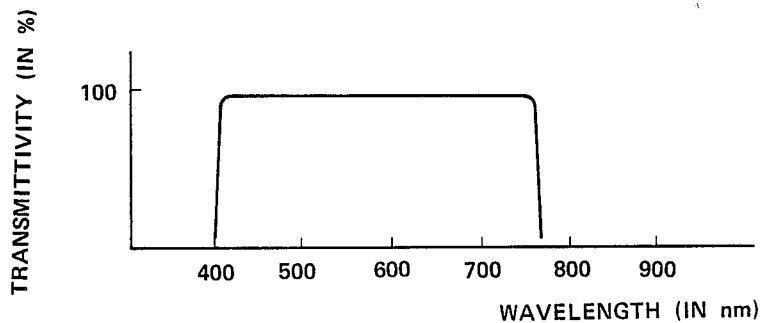

That is to say, as shown in FIG. 35, the filter 351a will transmit a narrow band with 569 nm. as a center and a narrow band with 650 nm. as a center. As shown in FIG. 36, the filter 351b will transmit a narrow band with 805 nm. as a center and a wavelength above 900 nm. As shown in FIG. 37, the filter 351c will transmit a narrow band near 580 nm., narrow band near 650 nm. and narrow band near 800 nm. As shown in FIG. 38, the filter 451d will transmit a band having a width of about 80 nm. with about 400 nm. as a center. As shown in FIG. 39, the filter 351e will transmit a visible band of about 400 to 750 nm.

The above mentioned band pass filter turret 351 will be rotated by a motor 352 controlled in the rotation by a filter switching apparatus 355. The above mentioned filter switching apparatus 355 will be controlled by a controlling signal from the switching circuit 343. When the observed wavelength is selected by the above mentioned switching circuit 343, the motor 352 will be rotated so that the filter corresponding to the observed wavelength selected by the above mentioned switching circuit 343 among the respective filters 351a to 351e of the above mentioned band pass filter turret may be interposed in the illuminating light path and the position in the rotating direction of the above mentioned band pass filter turret 351 will be changed.

The image of the object illuminated by the above mentioned illuminating light will be formed on the imaging surface of a solid state imaging device 203 by the objective lens 208. In such case, colors will be separated into G, Cy and Ye by the color filter array 202 but the wavelength will be limited by the above mentioned band pass filter turret 351.

The above mentioned solid state imaging device 203 will be read out by the application of a driving signal of the driver 220. The output signal of the above mentioned solid state imaging device 203 will be amplified by a pre-amplifier 222 and then will be transmitted through low path filters (LPF) 223 and 224 and a band pass filter (BPF) 225 within the video processor 6.

The above mentioned LPF's 223 and 224 will show cut-off characteristics, for example, of 3 MHz and 0.8 MHz and the signals transmitted respectively through them will be divided into a luminance signal YH in the high range and a luminance signal YL in the low range, will be input respectively into processing circuits 226 and 227 and will have γ corrected. The luminance signal YH on the high range side transmitted through the above mentioned processing circuit 226 will have the horizontal outline corrected and the horizontal aperture corrected and then will be input into a color encoder 229. The luminance signal YL on the low range side transmitted through the processing circuit 227 will be input into a matrix circuit 231 and correcting circuit 233 and will have to tracking corrected.

On the other hand, the signal will be passed through the BPF 225 of the passing band of 3.58±0.5 MHz to have the color signal component extracted. This color signal component will be input into a 1 HDL (1H delay line) 234, adder 235 and subtractor 236 to have the color signal components B and R separated and extracted. By the way, in this case, the output of the 1 HDL 234 will be processed by the processing circuit 227 and further will be mixed in a mixer 238 with the luminance signal YL on the low range side having had the vertical aperture corrected by a vertical correcting circuit 237 and this mixed output will be input into the above mentioned adder 235 and subtractor 236. The color signal B of the adder 235 and the color signal R of the subtractor 236 will be input respectively into γ-correcting circuits 241 and 242 to have γ corrected by using the luminance signal YL on the low range side transmitted through a correcting circuit. 233, will be input respectively into demodulators 243 and 244 to be made demodulated color signals B and R which will be then input into the matrix circuit 231. Color difference signals R-Y and B-Y will be produced by this matrix circuit 231 and then will be input into a color encoder 229. A luminance signal obtained by mixing the luminance signals YH and YL and a chromatic signal obtained by rectangularly intersecting and modulating the color difference signals R-Y and B-Y by a subcarrier will be mixed (further a synchronous signal not illustrated will be superimposed) and a composite video signal will be output from an NTSC output end 245. The observed part will be video-displayed in colors by the video signal output from this output end 245.

By the way, a synchronous signal will be input into the driver 220 from a synchronous signal generating circuit 252 and a driving signal synchronized with this synchronous signal will be output. The output of this synchronous signal generating circuit 252 will be input into a pulse generator 253 which will output various timing pulses.

In this embodiment, the filter switching apparatus will be controlled by a switching circuit 343. When one of respective filters 351a to 351e of a band pass filter turret 351 is selectively interposed in the illuminating light path, the wavelength range of the light passing through the above mentioned color filter array 202 will be further limited by this selected filter.

When the filter 351a is selected, the narrow ban with 650 nm. as a center will pass through the Ye transmitting filter and the narrow band with 569 nm. as a center will pass through the G transmitting filter. The object image by these two narrow bands will be imaged by the solid state imaging device 203.

Figure 33:
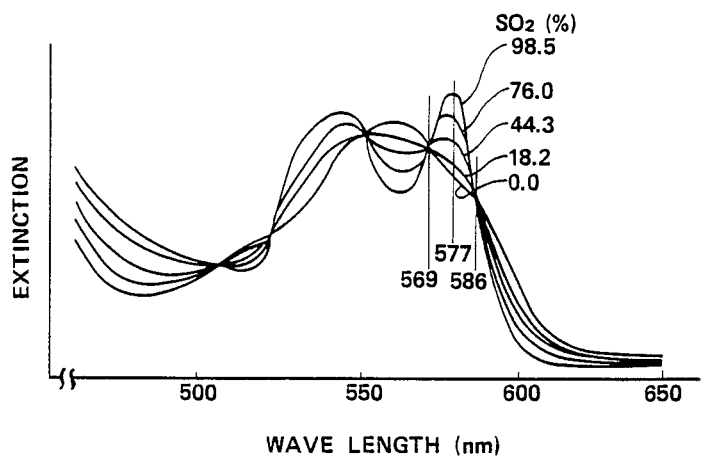

Now, the variation of the extinction (scattered reflection spectrum) of a blood by the variation of the oxygen saturation degree (mentioned also as $SO_2$) of hemoglobin is shown in FIG. 33. As shown in this diagram, 569 nm. is a wavelength at which the extinction of the blood will not substantially vary with the variation of $SO_2$ and 650 nm. is a wavelength at which the extinction of the blood will vary little (little as compared with the degree of the variation near 569 nm.) with the variation of $SO_2$. Therefore, the blood flow amount in the mucous membrane can be observed from the difference in the extinction between these wavelengths. By the way, as understood from FIG. 33, for the wavelength at which the extinction of the blood will not substantially vary with the variation of $SO_2$, 548.5 nm. and 586 nm. may be used instead of 569 nm.

When the filter 351b is selected a narrow band with 805 nm. as a center will pass through the Cy transmitting filter of the color filter array 202 and a band above 900 nm. will pass through the G transmitting filter. The object image by these two bands will be imaged by the solid state imaging device 203.

Now, the blood mixed with ICG (Indocyanine green) which is an infrared ray absorbing color will have a maximum absorption at 805 nm. and will show substantially no absorption rate above 900 nm. Therefore, when the above mentioned ICG is mixed into the blood, for example, by venous injection, with a picture image in the wavelength range of the above mentioned 805 nm. and above 900 nm., the vein running state below the mucous membrane will be able to be observed. That is to say, when an infrared light high in the transmittivity through the tissue is used, the light will be able to reach the deep part of the tissue and, on the other hand, in the Picture image in the wavelength range of 805 nm., the vein part will become a shade. Therefore, by taking the difference between this picture image in the wavelength range of 805 nm. and the picture image in the wavelength range above 900 nm., the vein running state can be made a video image at a high contrast.

When the filter 351c is selected, the narrow band near 650 nm. will pass thought the Ye transmitting filter of the color filter array 202, a narrow band near 580 nm. will pass through the G transmitting filter and a narrow band near 800 nm. will path through the Cy transmitting filter. The object image by these three narrow bands will be imaged by the solid state imaging device 203.

Figure 34:
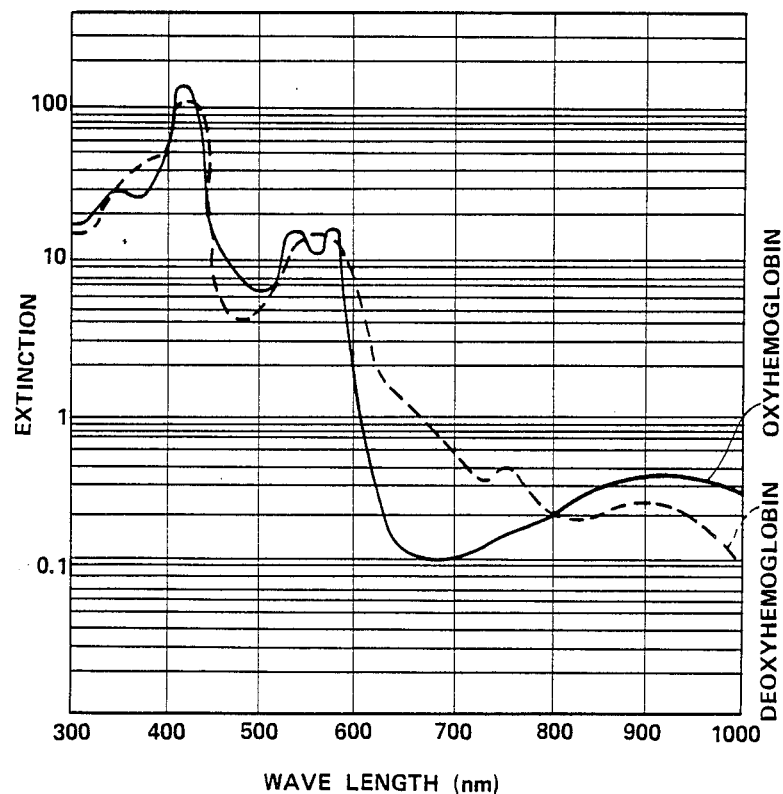

In FIG. 34, the spectral characteristics of oxyhemoglobin and deoxyhemoglobin are shown to show the variation of the extinction of a blood with the variation of $SO_2$. As shown in this diagram, the vicinities of 580 nm. and 800 nm. are ranges in which the extinction of the blood will not substantially vary with the variation of $SO_2$ and the vicinity of 650 nm. is a range in which the extinction of the blood will vary with the variation of $SO_2$. Therefore, by the picture image by these three wavelength ranges, the variation of $SO_2$ can be observed.

When the filter 351d is selected, the band near 400 nm. will pass through the Cy transmitting filter of the color filter array 202 and the object image by this band will be imaged by the solid state imaging device 203.

As shown in FIG. 34, the vicinity of 400 nm. is a range in which the extinction of hemoglobin is large. Therefore, by the picture image of this wavelength range near 400 nm., the hemoglobin distribution on the mucous membrane surface will be able to be observed at a high contrast.

When the filter 351e is selected, the transmitted wavelength ranges of the Cy and G transmitting filters of the color filter array 202 will be limited to only the visible light and the ordinary color picture image in the visible band will become observable.

Thus, according to this embodiment, when one of the respective filters 351a to 351e of the band pass filter turret is interposed in the illuminating light path, the ordinary picture image and the respective picture images showing the variations of the oxygen saturation degree of hemoglobin in the blood, blood flow amount, vein running state and hemoglobin amount will be able to be switched and observed.

By the way, in the ninth embodiment, the simultaneous type is used for the color imaging system but, even in the frame sequential type, in the same manner, by using the band pass filter turret 351, the color picture image in the ordinary visible range and the special picture image can be switched and observed. The example shall be explained in the tenth embodiment.

Figure 41:
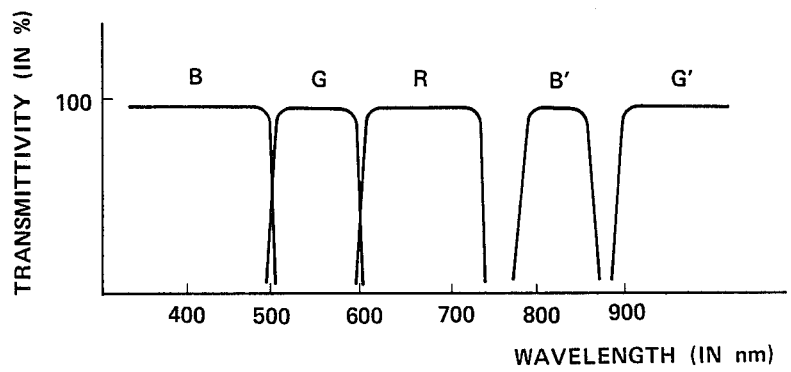
FIGS. 40 to 42 relate to the tenth embodiment of the present invention.
Figure 40:
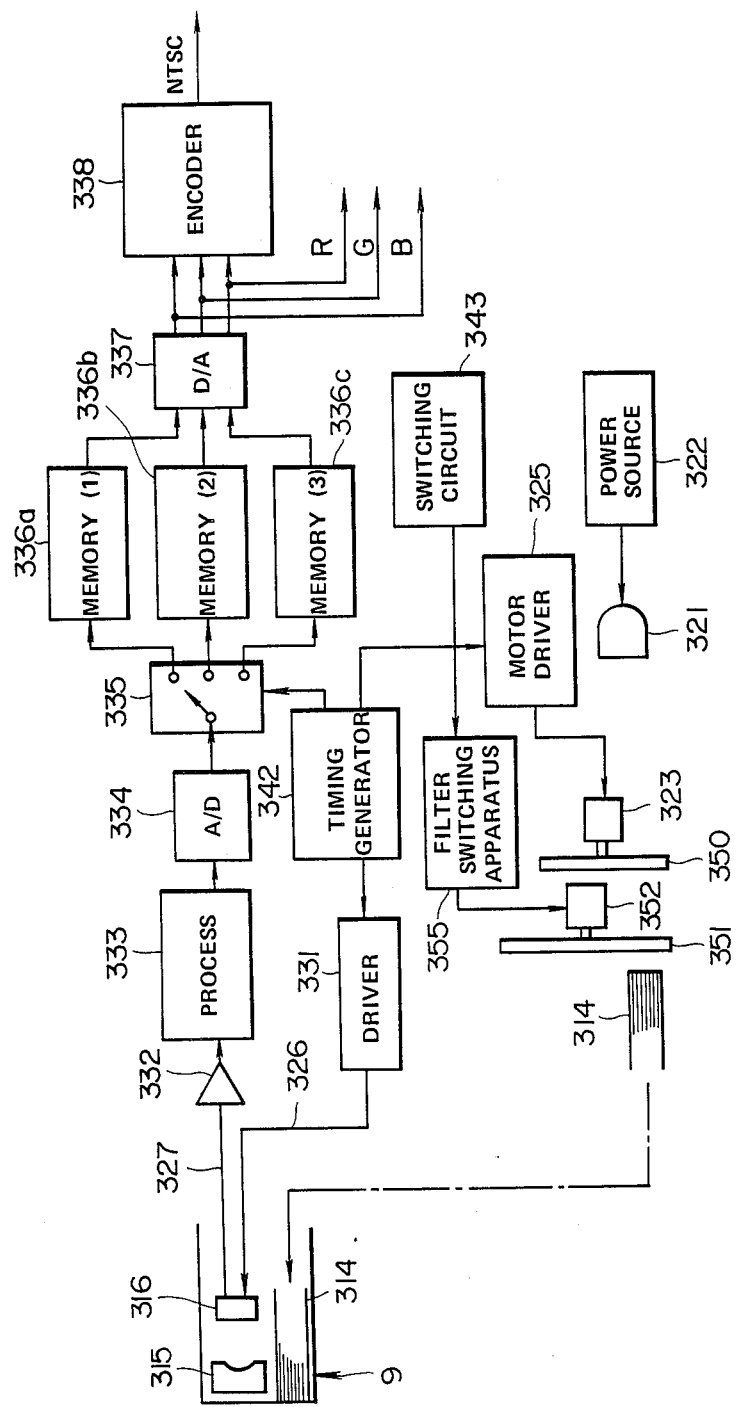
Figure 42:
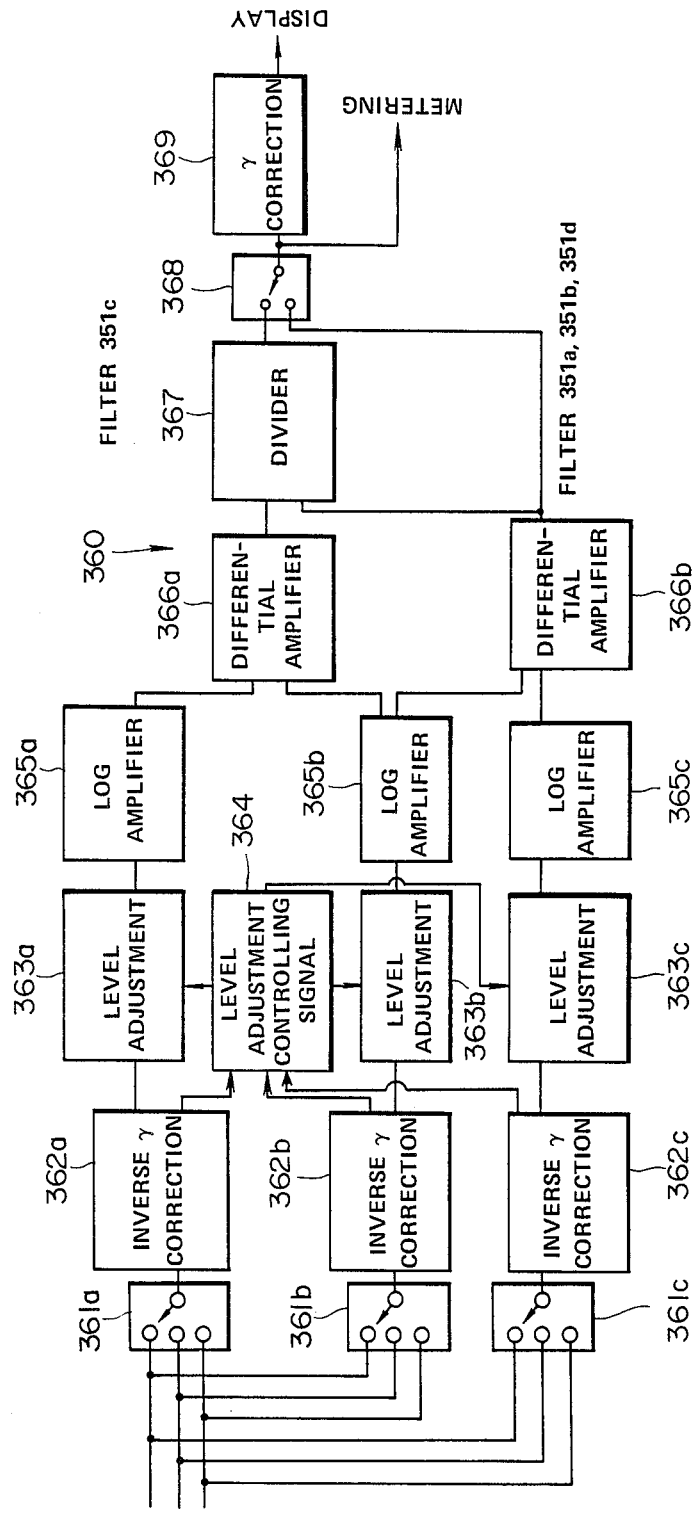

FIGS. 40 to 42 show the tenth embodiment of the present invention.

As shown in FIG. 40, a light guide 314 transmitting an illuminating light is inserted through an insertable part 2 of an electronic endoscope 1. The tip surface of this light guide 314 is arranged in the tip part 9 of the insertable part 2 so that the illuminating light may be emitted from this tip part 9. The above mentioned light guide 314 is inserted on the entrance end side through a universal cord 4 and is connected to a connector 5. An objective lens system 315 is provided in the above mentioned tip part 9 and a solid state imaging device 316 is provided in the image forming position of this objective lens system 315 and has a sensitivity in a wide wavelength range including the visible range and from the ultraviolet range to the infrared range. Signal lines 326 and 327 are connected to the above mentioned solid state imaging device 316, are inserted through the above mentioned insertable part 2 and universal cord 4 and are connected to the above mentioned connector 5.

On the other hand, a lamp 321 emitting a light in a wide range from the ultraviolet light to the infrared light is provided within the video processor 6. A general xenon lamp or strobo-lamp can be used for this lamp 321. The above mentioned xenon lamp or strobo-lamp will emit large amounts of not only the visible light but also the ultraviolet light and infrared light. This lamp 321 will be fed with an electric power by a power source 322. A rotary filter 350 rotated and driven by a motor 323 is arranged forward of the above mentioned lamp 321. Filters transmitting the lights of the respective wavelength ranges of red (R), green (G) and blue (B) for the ordinary observation are arranged in the peripheral direction on this rotary filter 350>. The transmission characteristics of the respective filters of this rotary filter 350 are shown in FIG. 41. As shown in this diagram, in this embodiment, the filter transmitting B has a characteristic of transmitting a wavelength range B' near 800 nm. and the filter transmitting G has a characteristic of transmitting a wavelength range G' above about 900 nm.

The above mentioned motor 323 will be driven as controlled in the rotation by a motor driver 325.

Also, a band pass filter turret 351 is arranged in the illuminating light path between the above mentioned rotary filter 350 and the entrance end of the light guide 314.

The same as in the eighth embodiment, this band pass filter turret 351 will be rotated by the motor 352 controlled in the rotation by a filter switching apparatus 355 and one of the filters 351a to 351e will be selectively interposed in the illuminating light path.

The light transmitted through the above mentioned rotary filter 350 and separated in time series into the lights of the respective wavelength ranges of R, G and B will further pass through the selected filter of the above mentioned band pass filter turret 351, will be input into the above mentioned light guide 314 a the entrance end, will be led to the tip part 9 through this light guide 314 and will be projected out of the tip part 9 to illuminate the part to be observed.

The returning light from the observed part by this illuminating light will be made to form an image on the solid state imaging device 316 by the objective lens system and will be photoelectrically converted. A driving pulse from a driver circuit 331 within the above mentioned video processor 6 will be applied to this solid state imaging device 316 through the above mentioned signal line 326 and a video signal will be read out and transferred by this driving pulse. The video signal read out of this solid state imaging device 316 will be input into a pre-amplifier 332 provided within the above mentioned video processor 6 or electronic endoscope 1 through the above mentioned signal line 327. The video signal amplified by this pre-amplifier 332 will be input into a processing circuit 333, will be processed for the $\gamma$ correction and white balance and will be converted to a digital signal by an A/D converter 334. This digital video signal will be selectively memorized in three of a memory (1) 336a, memory (2) 336b and memory (3) 336c corresponding to respective colors, for example, of red (R), green (G) and blue (B) by a selecting circuit 335. The signal of the above mentioned memory (1) 336a, memory (2) 336a and memory (3) 336c will be simultaneously read out, will be converted to analogue signals by a D/A converter 337 and will be output as R. G and B color signals or will be input into an encoder 338 and will be output from this encoder 338 as an NTSC composite signal.

Then, the above mention R, G and B color signals or NTSC composite signal will be input into the color monitor 7 and the observed part will be color-displayed by this color monitor 7.

A timing generator 342 for timing the entire system is provided within the above mentioned video processor 6 so that the respective circuits of the motor driver 325, driver circuit 331 and selecting circuit 335 may be synchronized by this timing generator 342.

In this embodiment, when a filter switching apparatus 355 is controlled with a switching circuit 343 and one of respective filters 351a to 351e of a band pass filter turret 351 is selectively interposed in the illuminating light path, the wavelength range of the light transmitted through the above mentioned rotary filter 350 will be further limited by this selected filter.

When the filter 351a is selected the narrow band with 650 nm. as a center will pass through the R transmitting filter at the timing when it is interposed in the illuminating light path and the narrow band with 569 mn. as a center will pass through the G transmitting filter at the timing when it is interposed in the illuminating light path. The lights of these two narrow bands will be radiated to an object respectively at the timings of R and G and the object images by these illuminating lights will be imaged by the solid state imaging device 316. The picture images of the above mentioned two wavelength ranges will be output respectively as picture images of R and G. From the difference of the extinction between these two wavelengths, the blood flow amount of the mucous membrane can be observed.

When the filter 351b is selected, the narrow band with 805 nm. as a center will pass through the B transmitting filter of the rotary filter 350 at the timing when it is interposed in the illuminating light path and the band above 900 nm. will pass through the G transmitting filter at the timing when it is interposed in the illuminating light path. The lights of these two band will be radiated to the object respectively at the timings of B and G and the object images by these illuminating lights will be imaged by the solid state imaging device 316. The picture images of the above mentioned two wavelength ranges will be output respectively as picture images of B and G.

By taking the difference between the picture image of the wavelength range of 805 nm. and the picture image of the wavelength range above 900 nm., the vein running state will be able to be made a video signal at a high contrast.

When the filter 351c is selected, the narrow band near 650 nm. will pass through the R transmitting filter of the rotary filter 350 at the timing when it is interposed in the illuminating light path, the narrow band near 580 nm. will pass through the G transmitting filter at the timing when it is interposed in the illuminating light path and the narrow band near 800 nm. will pass through the B transmitting filter at the timing when it is interposed in the illuminating light path. The lights of these three narrow bands will be radiated to the object respectively at the timings of R, G and B and the object images by these illuminating y lights will be imaged by the solid state imaging device 316. The picture images of the above mentioned three wavelength ranges will be output respectively as picture images of R, G and B.

By the picture images by these three wavelength ranges, the variation of $SO_2$ can be observed.

When the filter 351d is selected, the band near 400 nm. will path through the B transmitting filter of the rotary filter 350 at the timing when it is interposed in the illuminating light path. The light of this band will be radiated to the object at the timing of B, the object image by this illuminating light will be imaged by the solid state imaging device 316 and the picture image of this wavelength range will be output as a picture image of B.

By the picture image of the wavelength range near 400 nm., the hemoglobin distribution on the mucous membrane surface will be able to be observed at a high contrast.

When the filter 351e is selected, the wavelength ranges passing through the B and G transmitting filters of the rotary filter 350 will be limited to only the visible lights, the ordinary frame sequential lights of R, G and B will be radiated to the object and the object images by these illuminating lights will be imaged by the solid state imaging device 316. Therefore, the ordinary color picture image in the visible band will be able to be observed.

When the wavelength ranges are limited by the respective filters of the above mentioned band pass filter turret 351 and the picture image signals allotted to R, G and B are processed by such signal processing circuit 360 as is shown in FIG. 42, a picture image showing the $SO_2$ and hemoglobin amount will be above to be obtained.

The above mentioned signal processing circuit 360 has three selectors 361a, 361b and 361c of three inputs and one output. The picture image signals corresponding to the respective wavelengths will be applied respectively to the respective inputs of the respective selectors. The above mentioned respective selectors will select and output picture image signals corresponding to the wavelengths different from each other. The outputs of the above mentioned respective selectors will be input respectively into inverse $\gamma$ correcting circuits 362a, 362b and 362c and will be inversely $\gamma$-corrected to be returned to the original state as they have been already $\gamma$-corrected by the above mentioned video processor 6. The output of the above mentioned inversely $\gamma$-correcting circuit will be input respectively into level adjusting circuits 363a, 363b and 363c. In each level adjusting circuit, the level will be adjusted by the level adjusting controlling signal from a level adjusting controlling signal generating circuit 364. By the three level adjusting circuits 363, the entire level will be adjusted. Further, in such diagram sowing the variation of the extinction of the blood by the variation of the oxygen saturation degree as is shown, for example, in FIG. 34, as the ordinate is a logarithmic axis, the outputs of the above mentioned level adjusting circuits will be logarithmically converted respectively by logarithmic amplifiers 365a, 365b and 365c.

The outputs of the two logarithmic amplifiers 365a and 365b of the three logarithmic amplifiers will be input into a differential amplifier 366a so that the difference between the picture image signals corresponding to the two wavelengths may be computed. In the same manner, the outputs of the two logarithmic amplifiers 365b and 265c will be input into a differential amplifier 366b so that the difference between the picture images corresponding to the two wavelengths of the other combination may be computed.

In case the filter 351c of the above mentioned band pass filter turret 351 is selected, the difference between the picture image signal corresponding to the range in which the extinction of the blood will not substantially vary with the variation of $SO_2$ and the picture image signal corresponding to the range in which the extinction of the blood will vary with the variation of the $SO_2$ will be computed by the above mentioned differential amplifiers 366a and 366b and, from this difference, how much oxygen is dissolved in the examined object, that is, the oxygen saturation degree can be known.

The outputs of the above mentioned differential amplifiers 336a and 336b will be used to determine the oxygen saturation degree $SO_2$ and will be input into a divider 367. By making a predetermined computation by this divider 367, when the filter 351c is selected, the above mentioned $SO_2$ will be determined. When the filters 351a, 351b and 351d are selected, the output of the above mentioned differential amplifier 366b will be used to observe and measure respectively the variations of the blood flow amount, vein running state and hemoglobin amount. The output of the above mentioned divider 367 and the output of the differential amplifier 366b will be input into a selector 368 of two inputs so that either of the signal showing the $SO_2$ and the signal showing the blood flow amount, vein running state and hemoglobin amount may be selectively output from this selector 368.

In case the output signal of the above mentioned selector 368 is to be used for the measurement, it will be taken out as it is. On the other, in case the output signal is to be displayed, it will again have $\gamma$ corrected again and will be output in the monitor.

By the way, the signal processing circuit 360 shown in FIG. 42 is to compute as hardware but may make a process as software (that is, with a microcomputer).

Thus, in this embodiment, when one of the respective filters 351a to 351e of the band pass filter turret 351 is selectively interposed in the illuminating light path, an ordinary picture image and respective picture images showing the variations of the oxygen saturation degree of hemoglobin in the blood, blood flow amount, vein running state and hemoglobin amount will be able to be switched and observed.

By the way, in the ninth and tenth embodiments, the transmission characteristics and number of the respective filters of the band pass filter turret 351 as a wavelength limiting means can be freely set.

Also, as a wavelength limiting means, a plurality of filters having different transmission characteristics may be removably provided in the light path. The wavelength limiting means may be provided anywhere in the illuminating light path or observing light path leading to the imaging means such as on the front surface of the light guide exit end, in the image forming optical system, on the front surface of the solid state imaging device or in the course of the light guide.

The ninth and tenth embodiments can be applied not only to an electronic endoscope having a solid state imaging device in the tip part of an insertable part but also to such endoscope whereby a naked eye observation is possible as a fiber scope in the eyepiece part or an endoscope apparatus used as connected with a television camera in exchange for the above mentioned eyepiece part.

By the way, the present invention is not limited to the above mentioned respective embodiments. For example, the present invention is not limited to receive the reflected light of the observed object but may receive the light passing through the observed object.

Also, the present invention can be applied not only to a medical endoscope apparatus but also to an industrial endoscope apparatus.

It is apparent that, in this invention, working modes different in a wide range can be formed on the basis of this invention without deviating from the spirit and scope of the invention. This invention is not restricted by its specific working modes except being limited by the appended claims.

What is claimed is:

1. An endoscope apparatus comprising:
   An endoscope body having an elongate insertable part having an observing window in the tip part and an image forming optical system forming an object image by receiving a light returning from the object and entering through said observing window;
   an imaging means imaging the object image formed by said image forming optical system;
   a first wavelength range separating means separating the object image into images in a plurality of wavelength ranges in response to a simultaneous type color imaging system;
   a second wavelength range separating means separating the object image into images in a plurality of wavelength ranges of a combination different from said first wavelength range separating means, all pixels of said imaging means corresponding to this second wavelength range separating means being included in all pixels of said imaging means corresponding to said first wavelength range separating means;
   a signal processing means processing signals for said imaging means in response to the respective wavelength ranges separated by said first wavelength range separating means or said second wavelength range separating means; and
   a switching means switching said first wavelength range separating means and said second wavelength range separating means.

2. An endoscope apparatus according to claim 1 wherein said endoscope body further comprises an eyepiece part provided on the rear end side of said insertable part and an image transmitting means transmitting an object image formed by said image forming optical system to said eyepiece part and said imaging means is a television camera removably fitted to said eyepiece part.

3. An endoscope apparatus according to claim 1 further comprising an illuminating means feeding an illuminating means feeding an illuminating light to the observed visual field of said image forming optical system.

4. An endoscope apparatus according to claim 3 wherein said illuminating means has an illuminating window provided in the tip part of the insertable part of said endoscope body, a light source provided separately from said endoscope body and an illuminating light transmitting means transmitting an illuminating light emitted from said light source to said illuminating window.

5. An endoscope apparatus according to claim 1 wherein said second wavelength range separating means is a filter which can transmit a part of the wavelength range to be separated by said first wavelength range separating means and said switching means has a means of removably inserting the filter as said second wavelength range separating means between the illuminating light source and said imaging means.

6. An endoscope apparatus according to claim 5 wherein said first wavelength range separating means separates the visible light range into three wavelength ranges for obtaining color picture images.

7. An endoscope apparatus according to claim 6 wherein said second wavelength range separating means separates the wavelength range into a plurality of wavelength ranges including at least the wavelength range in which the variation of the extinction of a blood by the variation of the oxygen saturation degree of hemoglobin is large and the wavelength range in which the variation of the extinction of a blood by the variation of the oxygen saturation degree of hemoglobin is small.

8. An endoscope apparatus according to claim 6 wherein said second wavelength range separating means separates the wavelength range into a plurality of wavelength ranges including at least the wavelength range in which the infrared light absorption degree of an infrared light absorbing color is large and the wavelength range in which the infrared light absorption degree of an infrared light absorbing color is small.

9. An endoscope apparatus according to claim 1 wherein said imaging means is a solid state imaging device.

10. An endoscope apparatus according to claim 9 wherein said solid state imaging device is arranged in the image forming position of said image forming optical system.

11. An endoscope apparatus according to claim 9 wherein said second wavelength range separating means corresponds to a simultaneous type color imaging system and, in case this wavelength range separating means is used, a pixel information will be obtained from substantially all pixels of said imaging means.

12. An endoscope apparatus according to claim 11 further comprising a filter member integrating a filter as said first wavelength range separating means and a filter as said second wavelength range separating means and arrangeable so that in the first state, said first wavelength range separating means may be in the position corresponding to the photosensitive part of said solid state imaging device and said second wavelength range separating means may be in the position corresponding to the non-photosensitive part of said solid state imaging device and, in the second state, said second wavelength range separating means be in the position corresponding to the photosensitive part of said solid state imaging device and said first wavelength range separating means may be in the position corresponding to the non-photosensitive part of said solid state imaging device, said switching means having a moving means varying the relative optical position of said filter member and the photosensitive part of said solid state imaging device.

13. An endoscope apparatus according to claim 12 wherein said moving means uses piezoelectric oscillators.

14. An endoscope apparatus according to claim 12 wherein said first wavelength range separating means separates a visible light range into three wavelength ranges for obtaining a color picture image.

15. An endoscope apparatus according to claim 14 wherein said second wavelength range separating means separates the wavelength range outside the visible light range into a plurality of wavelength ranges.

16. An endoscope apparatus according to claim 1 wherein said first wavelength separating means separates in time series the object image into images in a plurality of wavelength ranges.

17. An endoscope apparatus according to claim 16 wherein said first wavelength range separating means is a filter transmitting also the light in the wavelength range to be separated by said second wavelength range separating means, said second wavelength range separating means is a filter provided removably between an illuminating light source and said imaging means and transmitting in turn the lights in a plurality of wavelength ranges and said switching means has a means of removably inserting the filter as said second wavelength range separating means between the illuminating light source and said imaging means.

18. An endoscope apparatus according to claim 17 wherein said first wavelength range separating means separates a visible light range into three wavelength ranges for obtaining color picture images.

19. An endoscope apparatus according to claim 18 wherein said second wavelength range separating means separates a wavelength range in which the variation of the extinction of a blood by the variation of the oxygen saturation degree of hemoglobin is large into a plurality of wavelength ranges.

20. An endoscope apparatus according to claim 18 wherein said second wavelength range separating means separates a wavelength range in which the variation of the extinction of a blood by the variation of the oxygen saturation degree of hemoglobin is small into a plurality of wavelength ranges.

21. An endoscope apparatus according to claim 18 wherein said second wavelength range separating means separates a part of the visible light range into a plurality of wavelength ranges.

22. An endoscope apparatus according to claim 21 wherein said second wavelength range separating means separates a green color light range into three wavelength ranges.

23. An endoscope apparatus according to claim 18 wherein said second wavelength range separating means separates a wavelength range outside the visible light range into a plurality of wavelength ranges.

24. An endoscope apparatus according to claim 23 further comprising a filter interposed between the illuminating light source and said imaging means in case said first wavelength range separating means is to be used and intercepting the wavelength range outside the visible range corresponding to said second wavelength range separating means.

25. An endoscope apparatus according to claim 23 wherein said second wavelength range separating means separates an infrared light range into three wavelength ranges.

26. An endoscope apparatus according to claim 23 wherein said second wavelength range separating means separates an ultraviolet light range into three wavelength ranges.

27. An imaging apparatus comprising:
an imaging means imaging an object image;
a first wavelength range separating means separating the object image into images in a plurality of wavelength ranges in response to a simultaneous type color imaging system;
a second wavelength range separating means separating the object image into images in a plurality of wavelength ranges of a combination different from said first wavelength range separating means, all pixels of said imaging means corresponding to this second wavelength range separating means being included in all pixels of said imaging means corresponding to said first wavelength range separating means;
a signal processing means processing signals for said imaging means in response to the respective wavelength ranges separated said first wavelength range separating means or said second wavelength range separating means; and
a switching means switching said first wavelength range separating means and said second wavelength range separating means.

28. An imaging apparatus comprising:
a solid state imaging device imaging an object image;
a filter member having a plurality of sets of optical members different from one another in the optical characteristics and arrangeable on the respective sets so that, when one set of optical members is in the position corresponding to the photosensitive part of said solid state imaging device, the other set of optical members may be in the position corresponding to the non-photosensitive part of said solid state imaging device; and
a moving means varying the relative optical positions of said filter member and the photosensitive part of said solid state imaging device.

* * * * *